(12) United States Patent
Masuda et al.

(10) Patent No.: US 8,518,067 B2
(45) Date of Patent: Aug. 27, 2013

(54) ULTRASONIC SURGICAL INSTRUMENT

(75) Inventors: Shinya Masuda, Hino (JP); Tadashi Kitayama, Sagamihara (JP); Yoshitaka Fujii, Atsugi (JP); Genri Inagaki, St Louis Park, MN (US)

(73) Assignee: Olympus Medical Systems Corp. (JP)

( * ) Notice: Subject to any disclaimer, the term of this patent is extended or adjusted under 35 U.S.C. 154(b) by 16 days.

(21) Appl. No.: 13/355,681

(22) Filed: Jan. 23, 2012

(65) Prior Publication Data
US 2012/0277778 A1 Nov. 1, 2012

Related U.S. Application Data

(63) Continuation of application No. PCT/JP2011/052907, filed on Feb. 10, 2011.

(60) Provisional application No. 61/303,715, filed on Feb. 12, 2010.

(51) Int. Cl.
*A61B 17/32* (2006.01)

(52) U.S. Cl.
USPC .......................................................... 606/169

(58) Field of Classification Search
USPC ................. 606/27, 45, 46, 48–52, 138–139, 606/142–145, 147–150, 167, 169, 205–211; 604/22; 227/175.1–182.1; 81/418, 419, 81/421–424, 424.5, 426, 426.5
See application file for complete search history.

(56) References Cited

U.S. PATENT DOCUMENTS 5,071,430 A * 12/1991 de Salis et al. ................ 606/219
5,217,460 A 6/1993 Knoepfler
5,322,055 A 6/1994 Davison et al.
5,397,324 A * 3/1995 Carroll et al. ................. 606/139
5,476,206 A * 12/1995 Green et al. ................ 227/176.1
6,024,750 A 2/2000 Mastri et al.
(Continued)

FOREIGN PATENT DOCUMENTS

EP    2 042 112      4/2009
JP    2001-524842    12/2001
(Continued)

OTHER PUBLICATIONS

Search Report issued by European Patent Office and received by applicant on Sep. 19, 2012 in connection with corresponding EP patent application No. EP 11 74 2314.
(Continued)

*Primary Examiner* — Ryan Severson
*Assistant Examiner* — David Eastwood
(74) *Attorney, Agent, or Firm* — Ostrolenk Faber LLP

(57) ABSTRACT

An ultrasonic surgical instrument includes an ultrasonic vibrator, a vibration transmission section, a grip member, a pad member provided at a position of the grip member which faces the treatment section, and a planar facing surface disposed on the pad member. A distal end portion of the treatment section faces the pad member, and is curved from a proximal end portion side of the treatment section toward the distal end portion side of the treatment section in a direction away from the facing surface. The pad member includes a protruding portion which is disposed on the facing surface, protrudes from the facing surface toward the distal end portion of the treatment section, and abuts on the distal end portion of the treatment section while the grip member is closed.

6 Claims, 21 Drawing Sheets

(56) References Cited

U.S. PATENT DOCUMENTS

| | | | |
|---|---|---|---|
| 7,264,618 B2* | 9/2007 | Murakami et al. | 606/27 |
| 7,306,599 B2* | 12/2007 | Karasawa et al. | 606/51 |
| 7,442,193 B2* | 10/2008 | Shields et al. | 606/49 |
| 7,909,824 B2* | 3/2011 | Masuda et al. | 606/51 |
| 2003/0135136 A1* | 7/2003 | Murakami | 601/2 |
| 2004/0097911 A1 | 5/2004 | Murakami et al. | |
| 2004/0243151 A1* | 12/2004 | Demmy et al. | 606/139 |
| 2005/0033337 A1* | 2/2005 | Muir et al. | 606/167 |
| 2006/0079879 A1 | 4/2006 | Faller et al. | |
| 2008/0015575 A1* | 1/2008 | Odom et al. | 606/51 |
| 2009/0048596 A1* | 2/2009 | Shields et al. | 606/51 |

FOREIGN PATENT DOCUMENTS

| | | |
|---|---|---|
| JP | 2008-272393 | 11/2008 |
| JP | 2009-082710 | 4/2009 |
| JP | 2009-082711 | 4/2009 |
| JP | 2010-005460 | 1/2010 |
| WO | WO 98/14126 | 4/1998 |
| WO | WO 03/095028 | 11/2003 |
| WO | WO 2007/143439 | 12/2007 |

OTHER PUBLICATIONS

International Search Report mailed Mar. 22, 2011 in corresponding PCT International Application No. PCT/JP2011/052907.

Written Opinion mailed Mar. 22, 2011 in corresponding PCT International Application No. PCT/JP2011/052907.

* cited by examiner

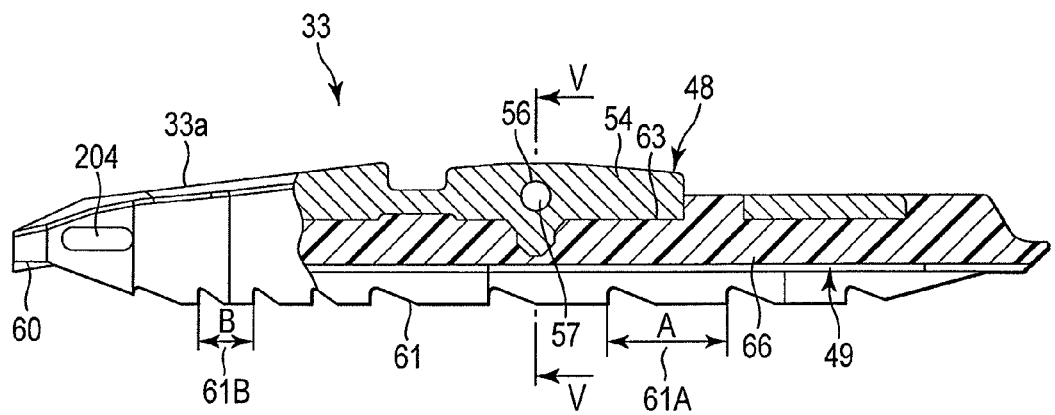
F I G. 4
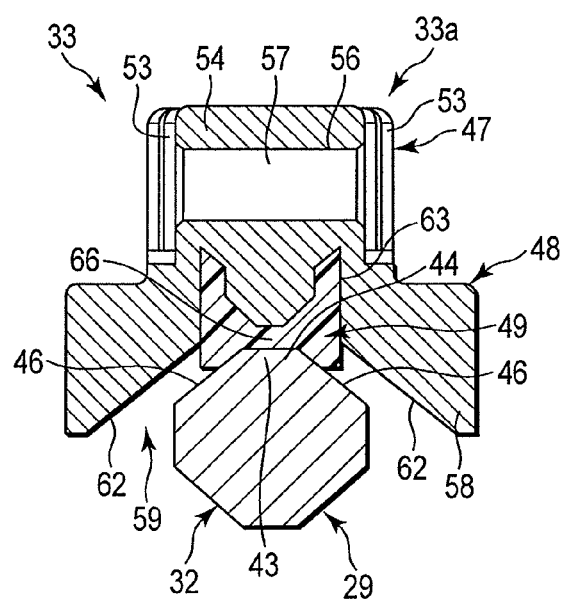
F I G. 5

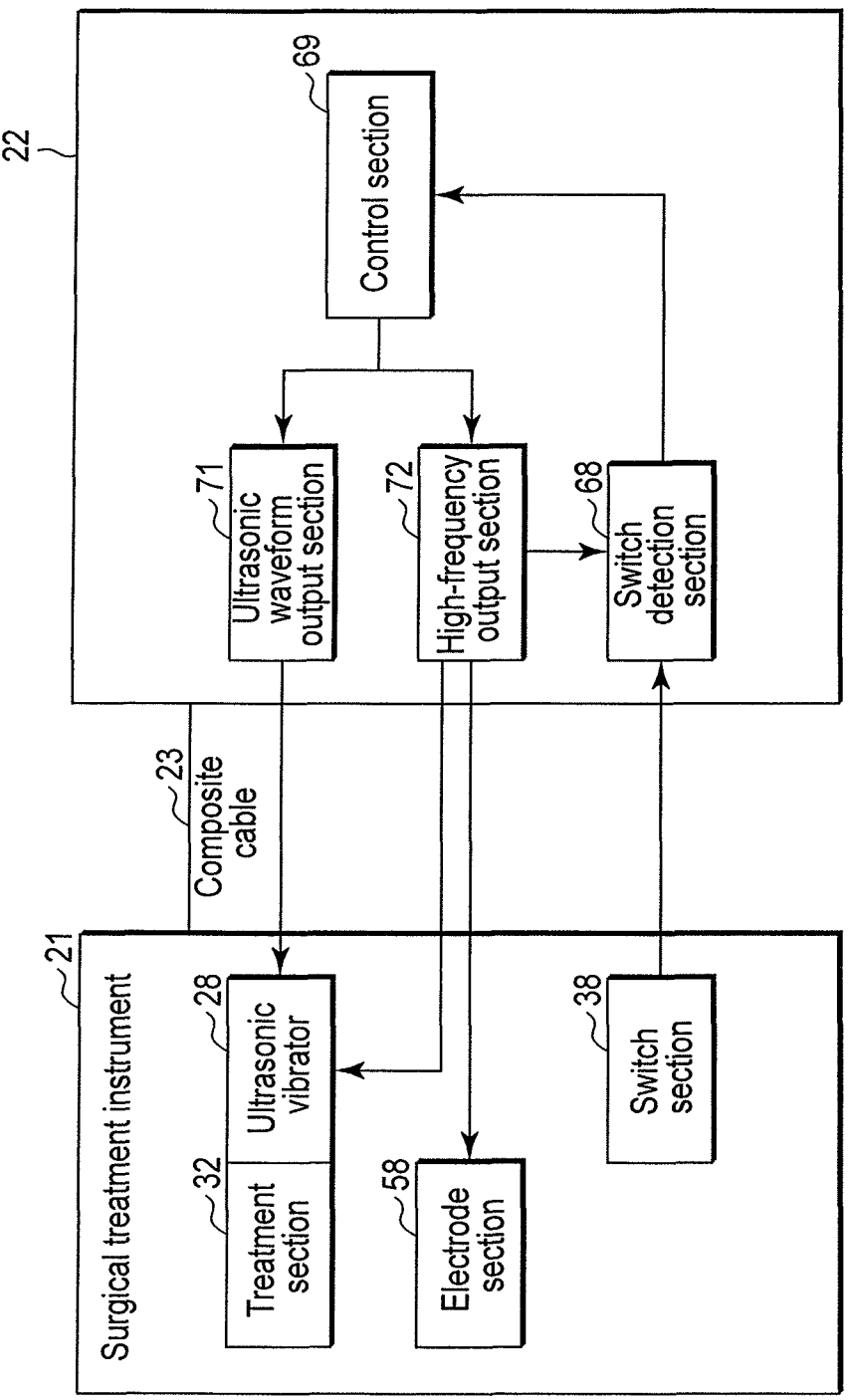
F I G. 6

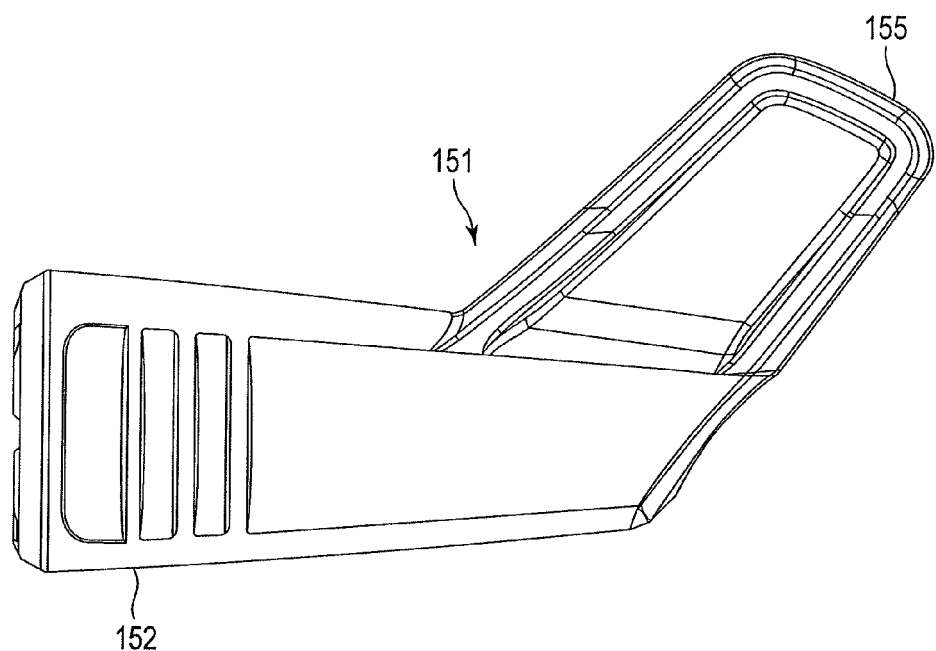
F I G. 10
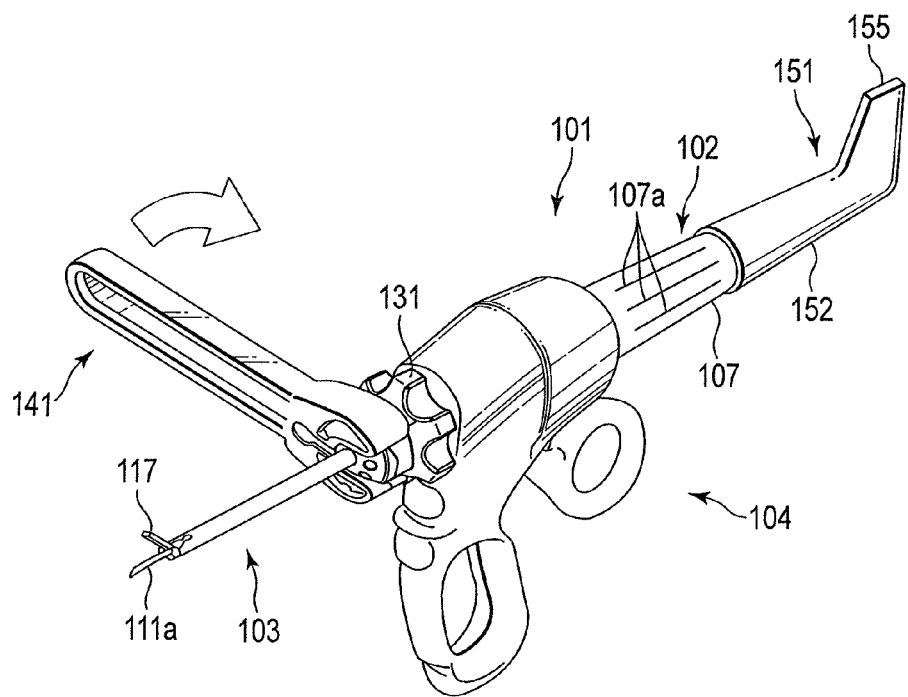
F I G. 11

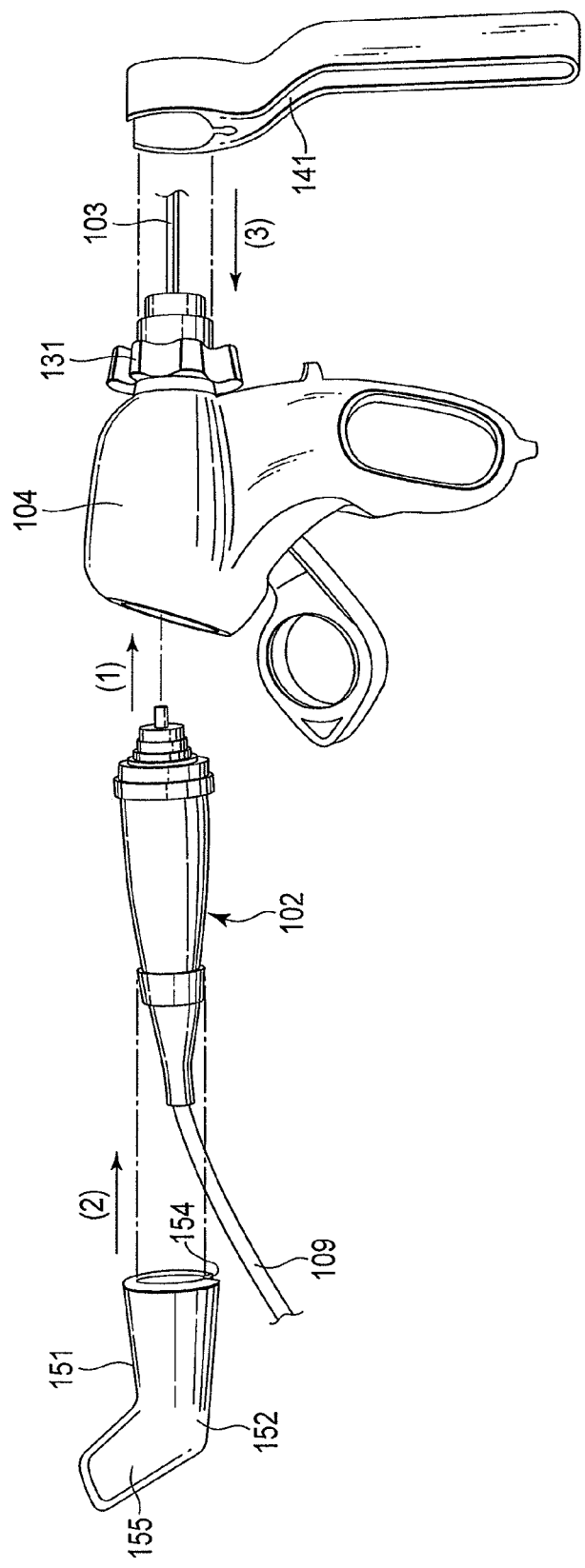
F I G. 12

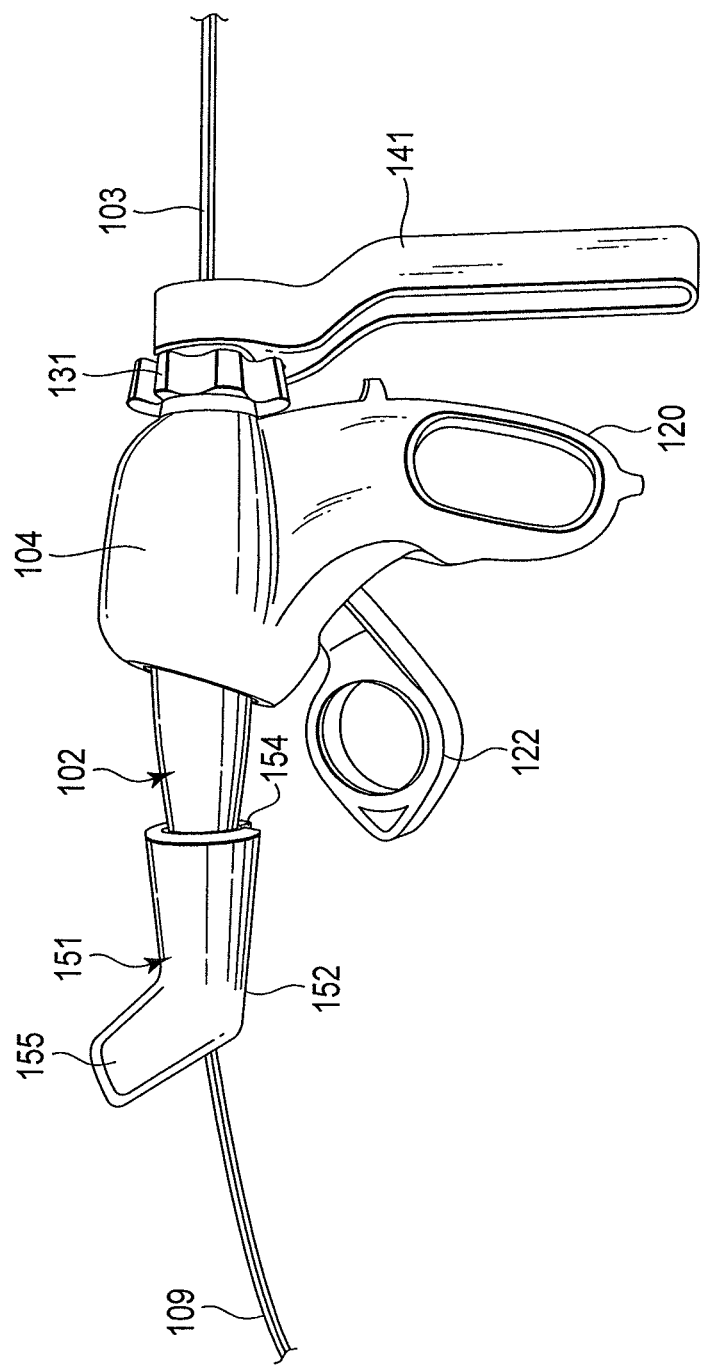
F I G. 13

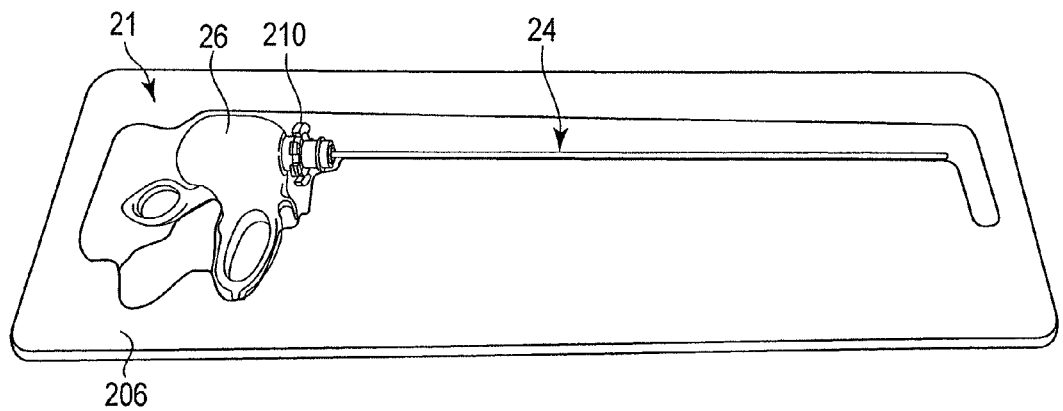
F I G. 15A
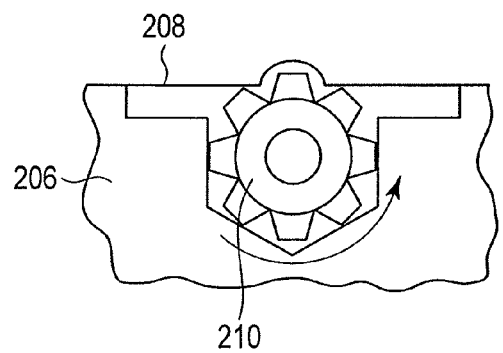
F I G. 15B
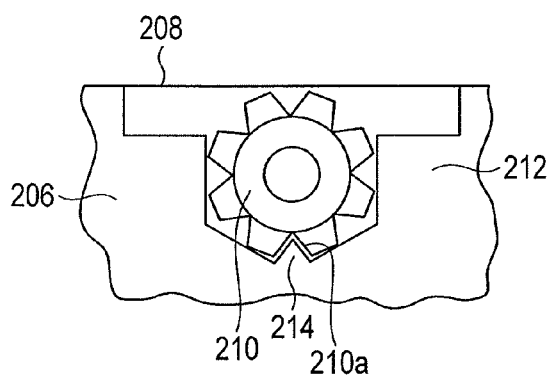
F I G. 15C

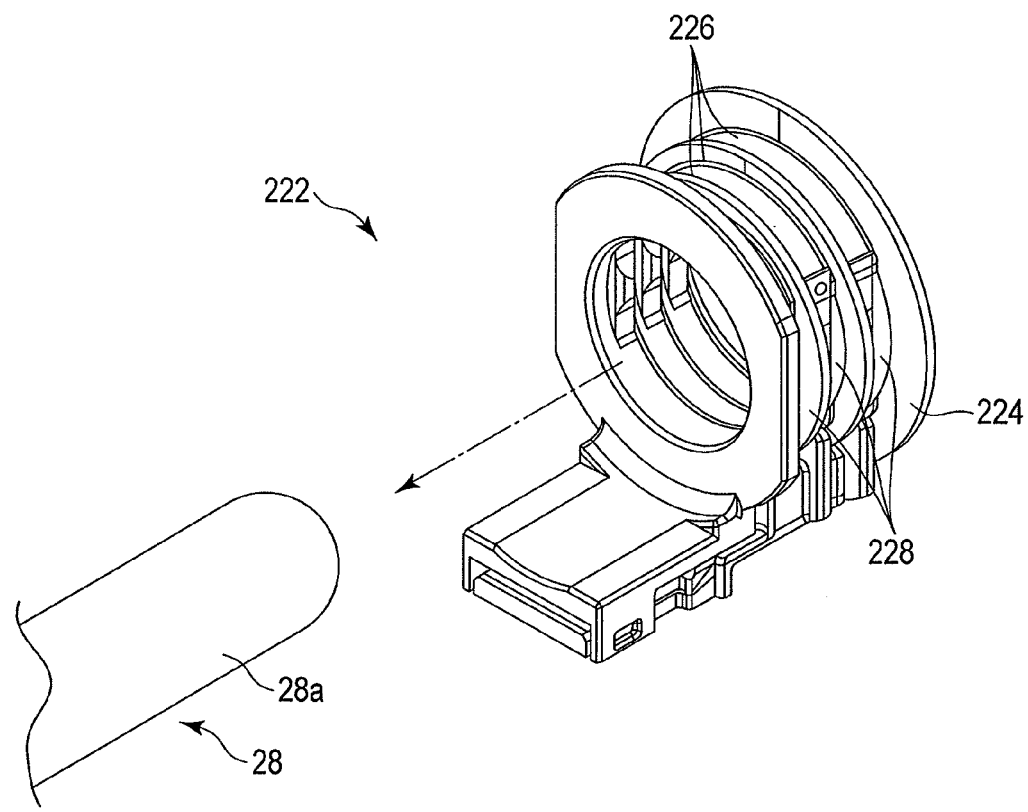
F I G. 16A
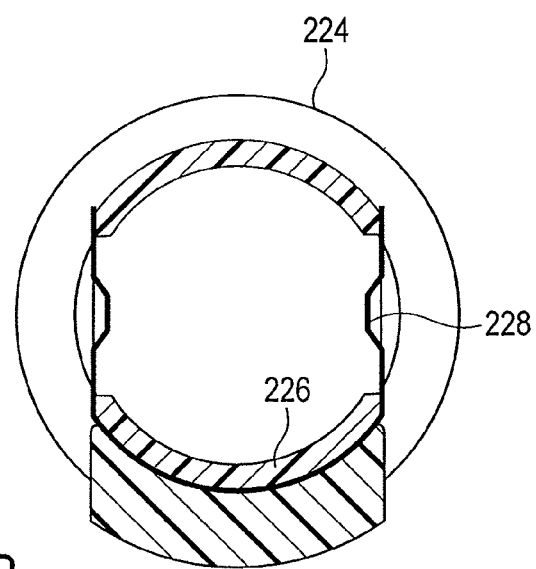
F I G. 16B

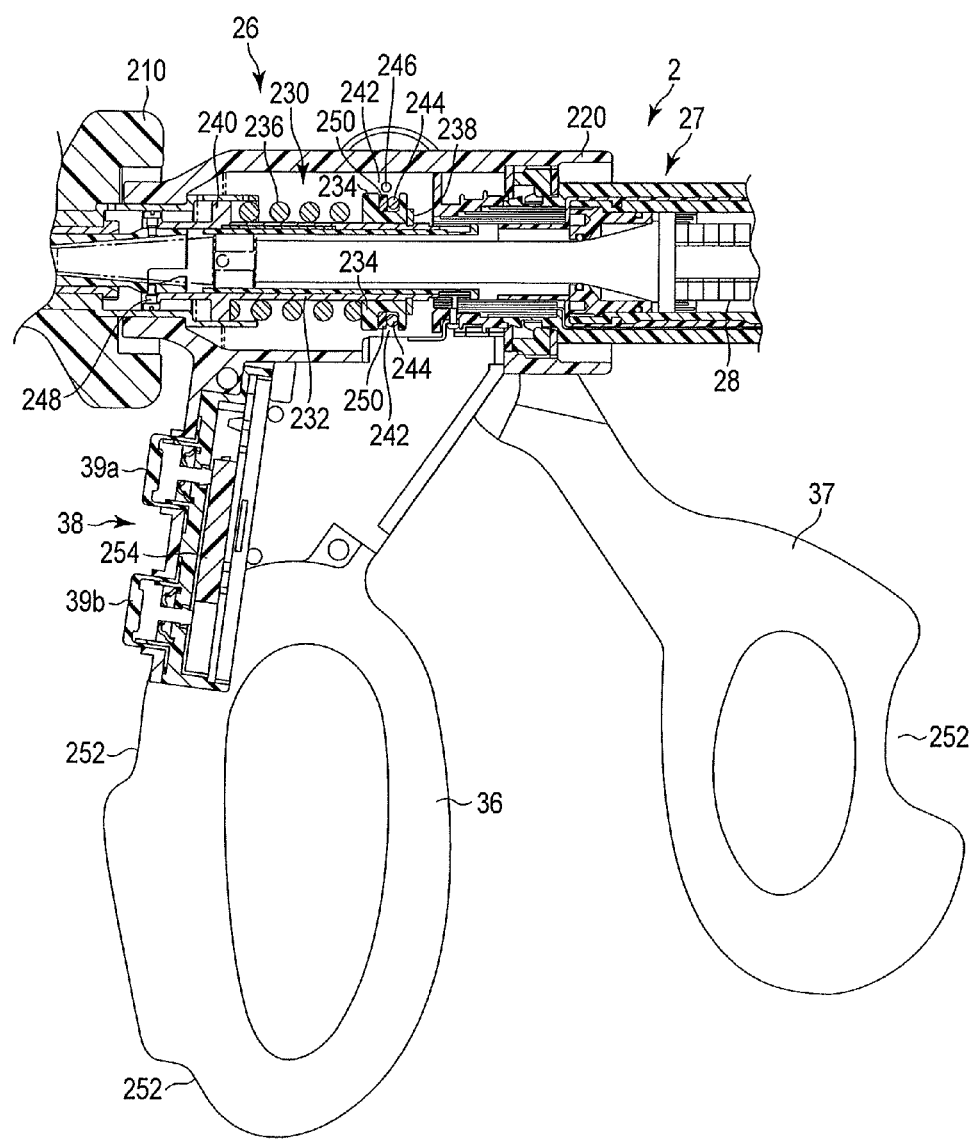
F I G. 17

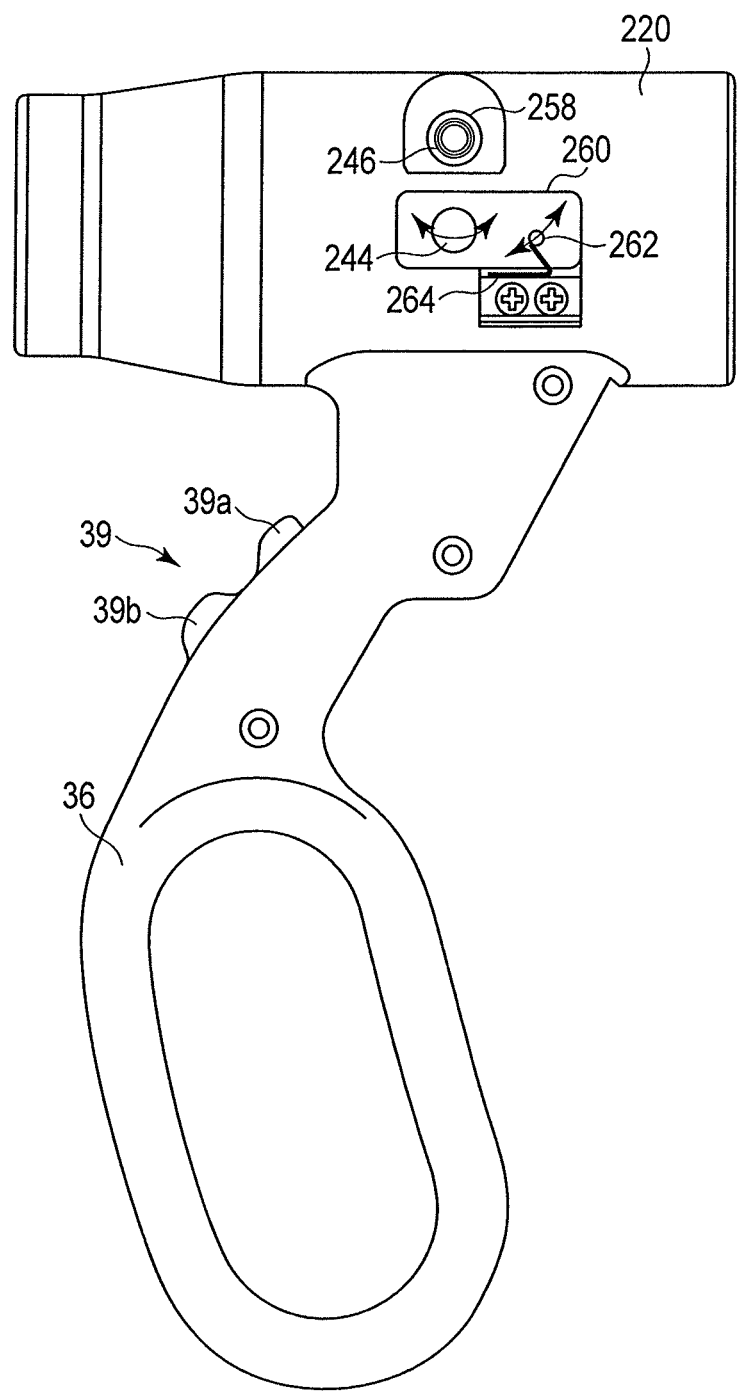
F I G. 18A

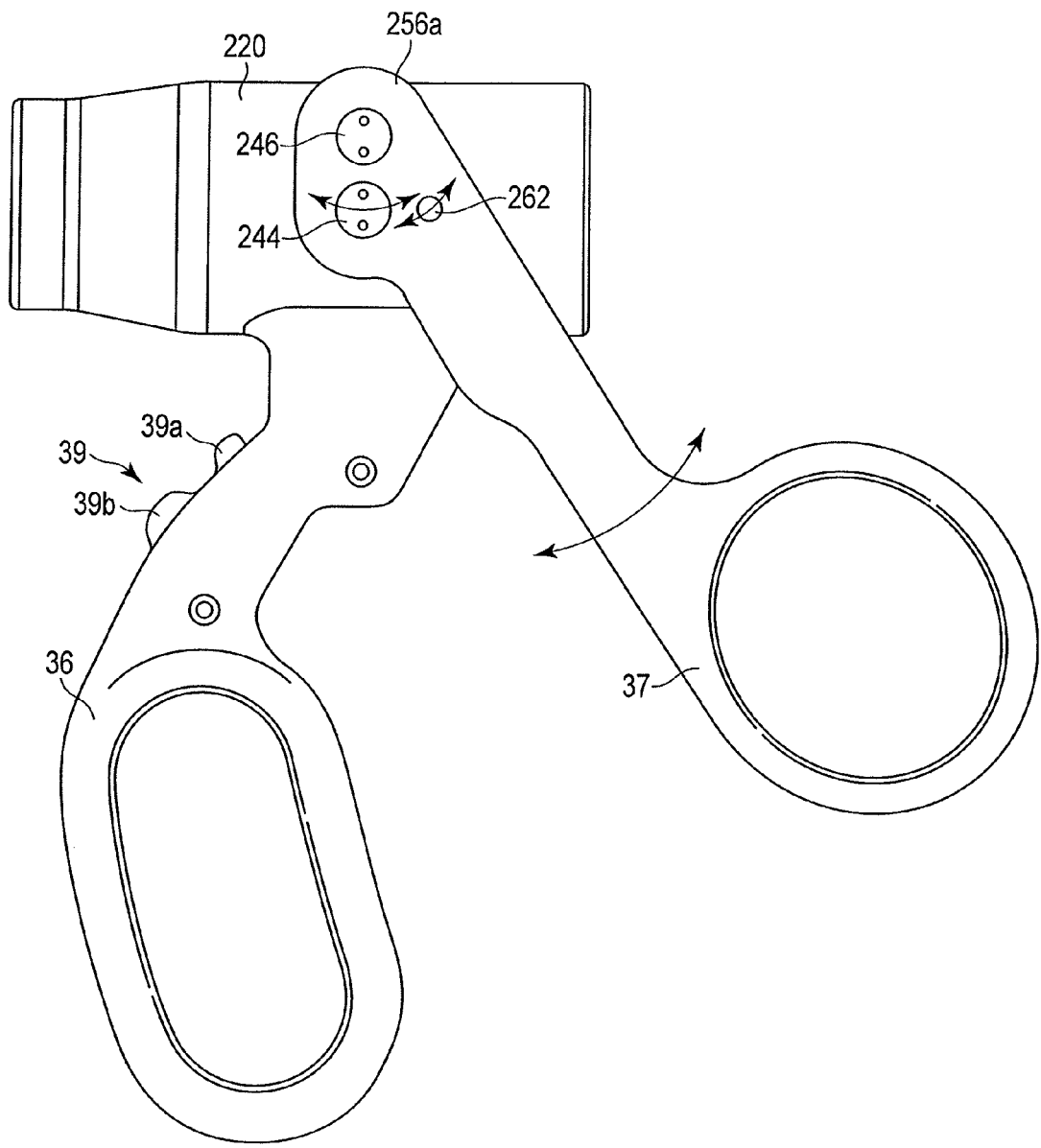
F I G. 18B

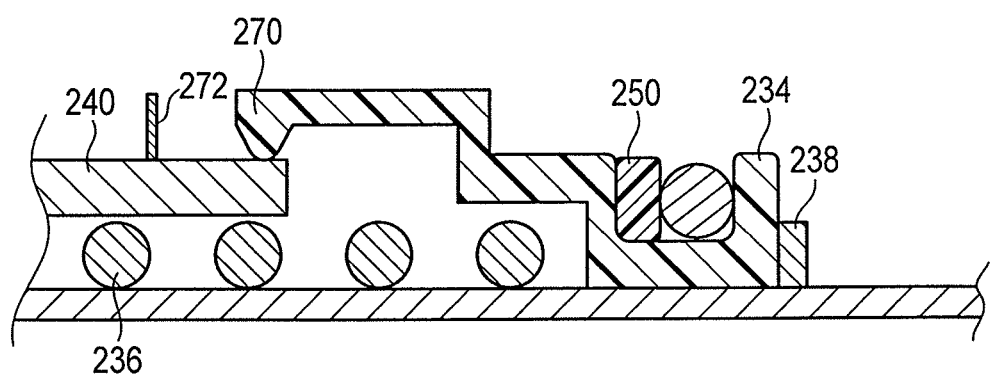
F I G. 20

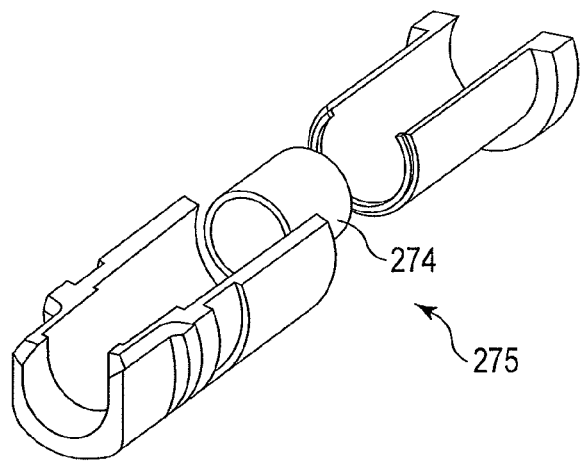
F I G. 21A
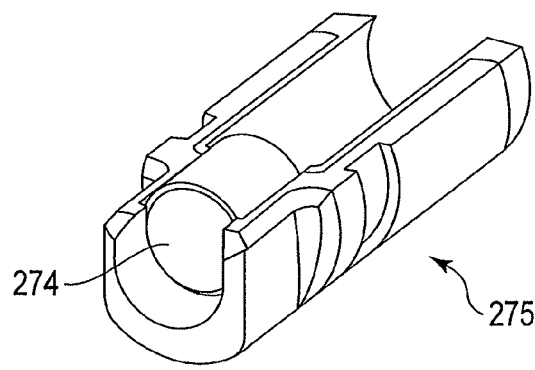
F I G. 21B
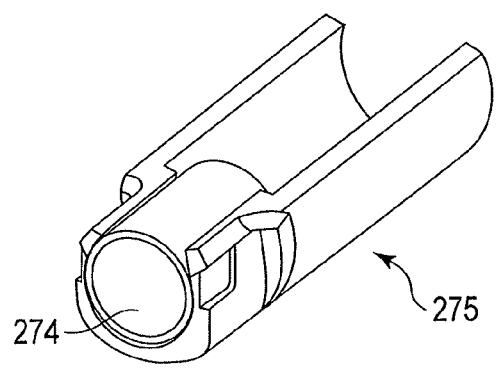
F I G. 21C

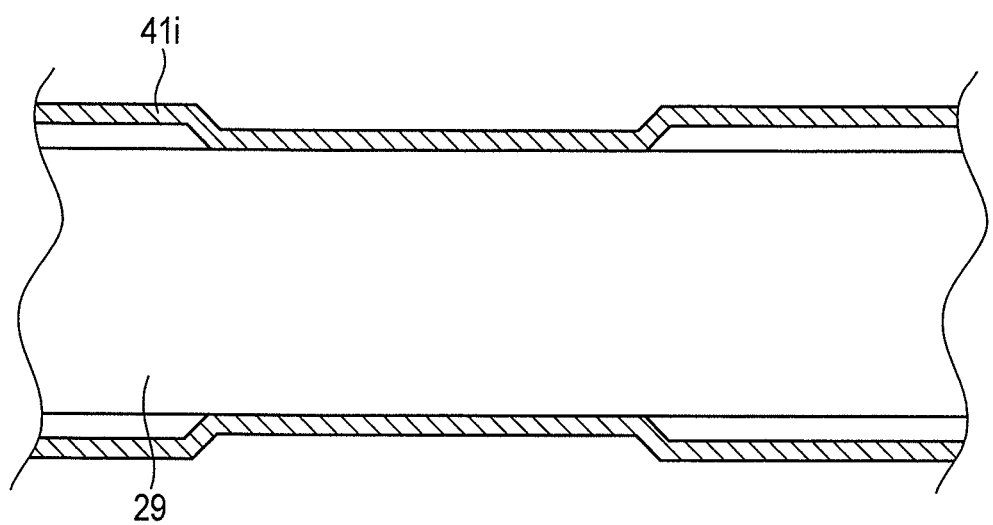
F I G. 22

ULTRASONIC SURGICAL INSTRUMENT

CROSS-REFERENCE TO RELATED APPLICATIONS

This application is a Continuation Application of PCT Application No. PCT/JP2011/052907, filed Feb. 10, 2011 and based upon and claiming the benefit of U.S. Provisional Application No. 61/303,715, filed Feb. 12, 2010, the entire contents of all of which are incorporated herein by reference.

BACKGROUND OF THE INVENTION

1. Field of the Invention

The present invention relates to an ultrasonic surgical instrument which uses ultrasonic vibration to treat living tissue.

2. Description of the Related Art

For example, Jpn. Pat. Appln. KOKAI Publication No. 2009-82711 has disclosed a surgical treatment instrument which uses ultrasonic vibration to treat living tissue. That is, in this surgical treatment instrument, a proximal end portion of a probe is coupled to an ultrasonic vibrator. The probe is inserted through an insertion sheath, and a distal end portion of the probe protrudes from a distal end portion of the insertion sheath to form a treatment section. On the other hand, a grip member that can be opened or closed relative to the treatment section is disposed in the distal end portion of the insertion sheath. The grip member is closed relative to the treatment section so that the living tissue can be gripped by the treatment section and the grip member. While the living tissue is gripped by the treatment section and the grip member, ultrasonic vibration generated by the ultrasonic vibrator is transmitted by the probe to ultrasonically vibrate the treatment section. Consequently, it is possible to carry out a coagulation/cutting treatment.

Moreover, for example, Jpn. Pat. Appln. KOKAI Publication No. 2009-82710 has disclosed a surgical treatment instrument similar to the surgical treatment instrument disclosed in Jpn. Pat. Appln. KOKAI Publication No. 2009-82711.

In the above-mentioned surgical treatment instrument, the grip member is opened or closed relative to the treatment section, whereby the living tissue is gripped by the grip member and the treatment section. A distal end portion side of the surface of the treatment section which faces at least the grip member is curved toward a central axis of a probe 29 for the enhancement of removing properties in the treatment section relative to the living tissue and for the decrease of cavitations in the treatment section. The distal end portion side is curved away from the grip member. Moreover, the grip member is linearly formed.

BRIEF SUMMARY OF THE INVENTION

According to an aspect of embodiments, an ultrasonic surgical instrument comprising: an ultrasonic vibrator configured to generate ultrasonic vibration; a vibration transmission section configured to transmit the ultrasonic vibration generated in the ultrasonic vibrator; a treatment section formed in a distal end portion of the vibration transmission section, and configured to transmit the ultrasonic vibration from the ultrasonic vibrator to living tissue; a grip member openably or closably provided relative to the treatment section; a pad member provided at a position of the grip member which faces the treatment section; and a planar facing surface disposed on the pad member, and disposed substantially parallel to a longitudinal direction of the treatment section while the grip member is closed, wherein a distal end portion of the treatment section faces the pad member, and is curved from a proximal end portion side of the treatment section toward the distal end portion side of the treatment section in a direction away from the facing surface, and the pad member includes a protruding portion which is disposed on the facing surface, protrudes from the facing surface toward the distal end portion of the treatment section, and abuts on the distal end portion of the treatment section while the grip member is closed.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a partial longitudinal sectional side view showing a grip member according to the first embodiment of the present invention;

FIG. 5 is a cross-sectional view showing the distal grip section according to the first embodiment of the present invention in a normal state;

FIG. 6 is a block diagram showing the surgical treatment system according to the first embodiment of the present invention;

FIG. 10 is a side view of the adapter;

FIG. 11 is a perspective view showing an assembling operation state of the surgical treatment instrument of Modification 1;

FIG. 12 is a perspective view showing a state of the surgical treatment instrument of modification 1 before assembled;

FIG. 13 is a perspective view showing an assembled state of the surgical treatment instrument of modification 1;

FIG. 15A is a view showing that the surgical treatment instrument is accommodated in a sterilization tray;

FIG. 15B is a view showing that a rotary knob contacts a rattle sheet;

FIG. 15C is a view showing that the rotary knob is accommodated in a recess portion;

FIG. 16A is a perspective view showing that a contact point unit is inserted into a contact point section;

FIG. 16B is a side view of an electrode holding section assembled with an electrode member;

FIG. 17 is a sectional view of a handle unit and sheath unit after engaged;

FIG. 18A is a view showing that a pin moves toward an elastic member with an opening/closing operation of a movable handle, to flip the elastic member;

FIG. 18B is a view showing that the pin moves with an opening/closing operation of an operation handle;

FIG. 20 is a view showing that a claw moves with the opening/closing operation of the movable handle, to flip a film;

FIG. 21A is an exploded perspective view of a probe presser regulating section;

FIG. 21B is a perspective view of the probe presser regulating section;

FIG. 21C is a view showing a modification of the probe presser regulating section; and FIG. 22 is a view showing that squeeze processing is performed toward a probe so that part of an inner sheath abuts on the probe.

DETAILED DESCRIPTION OF THE INVENTION

Figure 1:
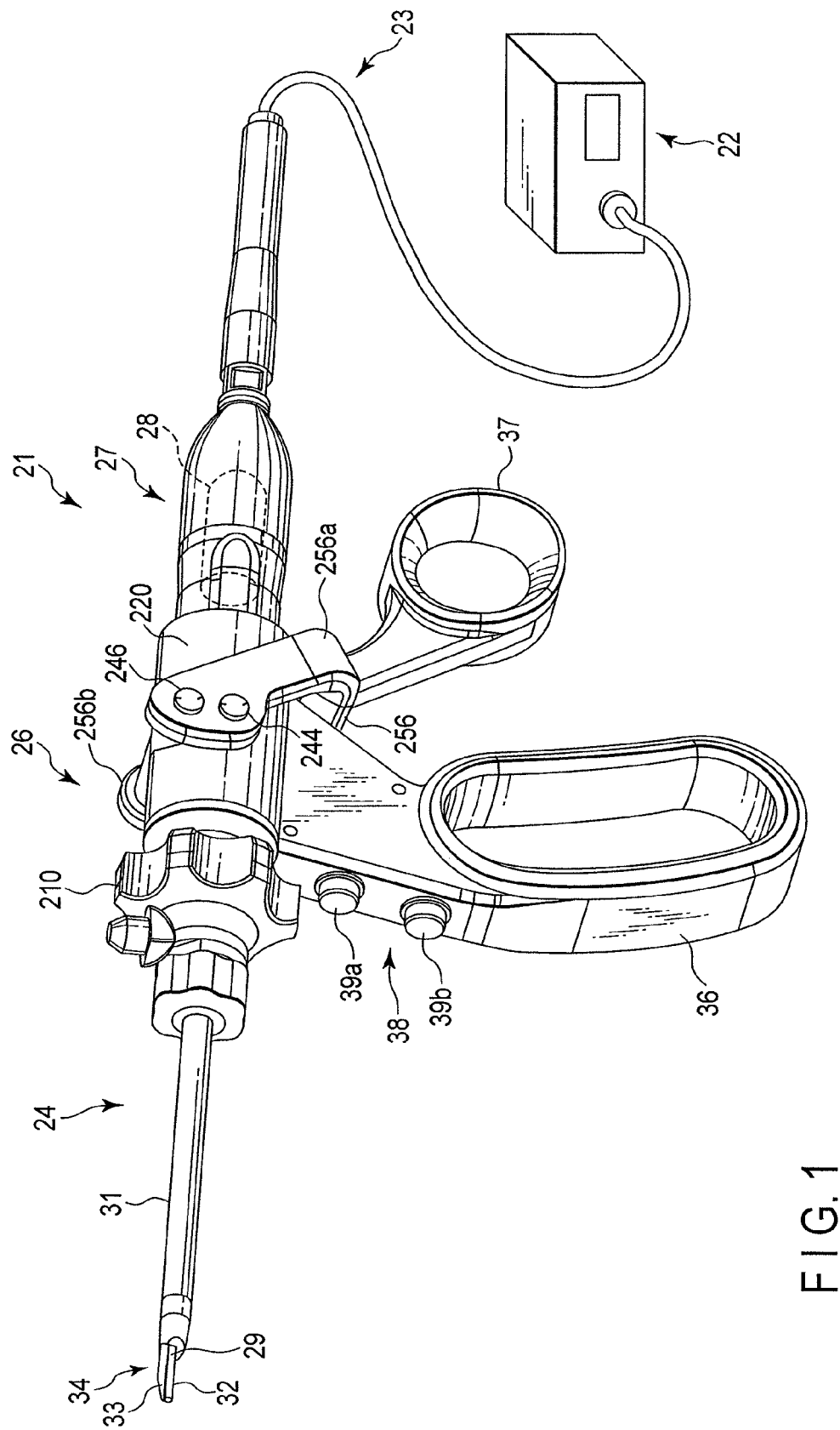
FIG. 1 is a perspective view showing a surgical treatment system according to a first embodiment of the present invention.

Embodiments of embodiments of the present invention will be described with reference to the drawings.

First Embodiment

The first embodiment of the present invention is described with reference to FIG. 1, FIG. 2, FIG. 3, FIG. 4, FIG. 5, FIG. 6, FIG. 7A, FIG. 7B, FIG. 8A and FIG. 8B.

A surgical treatment system is described with reference to FIG. 1.

The surgical treatment system according to the first embodiment uses both ultrasonic vibration and high-frequency current to carry out a surgical coagulation/cutting treatment on living tissue, and uses high-frequency current to carry out a surgical coagulation treatment on living tissue.

That is, the surgical treatment system includes a surgical treatment instrument 21 as a surgical treatment apparatus, for example, an ultrasonic surgical instrument configured to be held and operated by a surgeon. The surgical treatment instrument 21 is connected to an output device 22 via a composite cable 23 as a connector.

In the surgical treatment instrument 21, a handle unit 26 integral with a sheath unit 24, and a vibrator unit 27 are detachably connected from the distal side to the proximal side. A distal end portion of the handle unit 26 is coupled to a proximal end portion of the sheath unit 24. The vibrator unit 27 includes therein an ultrasonic vibrator 28 as a vibration generator. The ultrasonic vibrator 28 converts a drive signal input from the output device 22 to mechanical vibration, to generate ultrasonic vibration. A proximal end portion of a probe 29 as a vibration transmission section is coupled to the ultrasonic vibrator 28. The probe 29 is configured to axially transmit the ultrasonic vibration generated by the ultrasonic vibrator 28 from the proximal end portion to a distal end portion. The probe 29 is inserted through the handle unit 26 and the sheath unit 24.

In the sheath unit 24, the probe 29 is inserted through an insertion sheath 31. The distal end portion of the probe 29 protrudes from a distal opening of the insertion sheath 31, thus forming a treatment section 32. The treatment section 32 transmits the ultrasonic vibration transmitted from the probe 29 to the living tissue, and treats the living tissue by the ultrasonic vibration. A grip member 33 as a jaw is disposed in a distal end portion of the insertion sheath 31. The grip member 33 can open or close relative to the treatment section 32 in an opening/closing direction orthogonal to an axial direction of the probe. When the grip member 33 closes, the living tissue is sandwiched between the grip member and the treatment section 32, to grip the living tissue. Thus, a distal grip section 34 is formed by the treatment section 32 and the grip member 33.

The handle unit 26 is provided with a fixed handle 36 and a movable handle 37. If the movable handle 37 is turned relative to the fixed handle 36 in the handle unit 26, the grip member 33 is opened or closed relative to the treatment section 32 in the distal grip section 34. The fixed handle 36 is provided with a switch section 38. A cutting switch 39a and a coagulation switch 39b are provided in the switch section 38.

Figure 2:
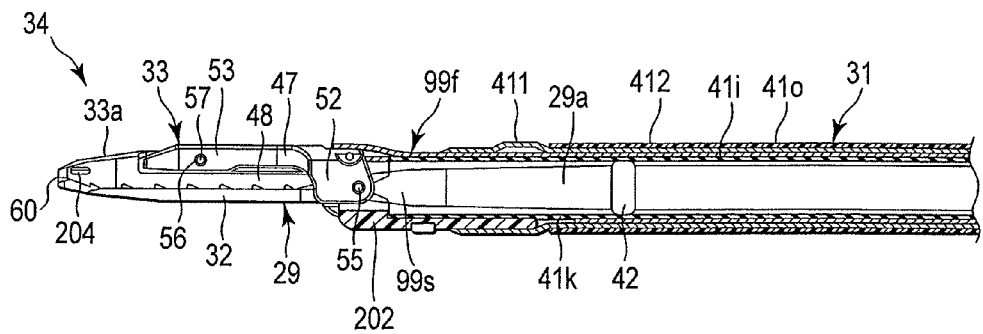
FIG. 2 is a partial longitudinal sectional side view showing a distal grip section according to the first embodiment of the present invention in a closed state.

In the surgical treatment system, as shown in FIG. 2, first and second electrical paths 99f and 99s used in a high-frequency treatment are formed from the output device 22 to the grip member 33 and the treatment section 32 of the surgical treatment instrument 21 via the composite cable 23, respectively.

When the cutting switch 39a of the handle unit 26 is depressed, a drive signal is output to the ultrasonic vibrator 28 from the output device 22. The ultrasonic vibrator 28 to which the drive signal is input generates ultrasonic vibration. The generated ultrasonic vibration is transmitted by the probe 29, and the treatment section 32 at the distal end portion of the probe 29 is ultrasonically vibrated. At the same time, a high-frequency voltage is applied between the grip member 33 and the treatment section 32 via the first and second electrical paths 99f and 99s by the output device 22.

On the other hand, when the coagulation switch 39b is depressed, no drive signal is output to the ultrasonic vibrator 28 from the output device 22, and a high-frequency voltage is applied between the grip member 33 and the treatment section 32 via the first and second electrical paths 99f and 99s by the output device 22.

The distal grip section 34 of the surgical treatment instrument 21 is described in detail with reference to FIG. 2, FIG. 3, FIG. 4, and FIG. 5.

As shown in FIG. 2, FIG. 3, FIG. 4 and FIG. 5, the insertion sheath 31 is formed by an outer sheath 41o and an inner sheath 41i. In the outer sheath 41o, the outside of a conductive metal pipe 411 is covered with an insulating resin tube 412. The inner sheath 41i is a conductive metal pipe. The inner sheath 41*i* and the probe 29 are insulated by an insulating tube 41*k*. The inner sheath 41*i* can be axially moved back and forth relative to the outer sheath 41*o*.

The probe 29 is made of a conductive material having high acoustic effects and biocompatibility, for example, a titanium alloy such as a Ti-6Al-4V alloy. In the probe 29, an insulating and elastic rubber lining 42 is equipped in the position of each node of the ultrasonic vibration. The rubber lining 42 is disposed between the inner sheath 41*i* and the probe 29 in a compressed state. The probe 29 is held to the inner sheath 41*i* by the rubber lining 42. A clearance is maintained between the inner sheath 41*i* and the probe 29. It is to be noted that the insulating tube is provided on the inner peripheral surface of the inner sheath 41*i*, and the rubber lining 42 abuts on the insulating tube 41*k*.

As shown by a cross-sectional surface which is orthogonal to the axial direction of the probe 29 in FIG. 5, an abutting portion 43 is formed by the part of the treatment section 32 facing the grip member 33. An abutting surface 44 is formed by one side surface of the abutting portion 43 facing the grip member 33. A pair of electrode surfaces 46 are formed by both side surfaces on both sides of the abutting surface 44.

The grip member 33 is formed by a body member 47, an electrode member 48, and a pad member 49.

The body member 47 is made of a hard and conductive material. As shown in FIG. 2, a proximal end portion of the body member 47 includes a pivot connection portion 52. The pivot connection portion 52 is pivotally connected to a distal end portion of the outer sheath 41*O* via a pivot connection shaft 55. The pivot connection shaft 55 extends in a width direction perpendicular to both the axial direction and the opening/closing direction. The body member 47 can turn about the pivot connection shaft 55 relative to the outer sheath 41*o*. A distal end portion of the inner sheath 41*i* is pivotally connected to the pivot connection portion 52 of the body member 47 at a position provided to the distal side and the opening-direction side of the pivot connection shaft 55.

When the movable handle 37 is turned relative to the fixed handle 36 in the handle unit 26, the inner sheath 41*i* is moved back and forth relative to the outer sheath 41*o*. Consequently, the body member 47 is driven by the inner sheath 41*i* to turn about the pivot connection shaft 55 relative to the outer sheath 41*o*.

On the other hand, a distal part of the body member 47 constitutes a pair of pivot bearings 53. The pair of pivot bearings 53 are in the form of plates which extend in the axial direction and which are perpendicular to the width direction, and are disposed apart from each other in the width direction.

The electrode member 48 is made of a hard and conductive material. The part of the electrode member 48 provided on the opening-direction side constitutes a pivot support 54. An insertion hole 56 is formed through the pivot support 54 in the width direction. A pivot support shaft 57 is inserted through the insertion hole 56 and extends in the width direction. The pivot support 54 is disposed between the pair of pivot bearings 53 of the body member 47, and is pivotally supported on the pair of pivot bearings 53 via the pivot support shaft 57. The electrode member 48 can oscillate about the pivot support shaft 57 relative to the body member 47. Further, the part of the electrode member 48 provided on the closing-direction side constitutes an electrode section 58. The electrode section 58 extends in the axial direction, and projects to both sides in the width direction. A recessed groove 59 which is open toward the closing direction extends in the axial direction in the part of the electrode section 58 provided on the closing-direction side. Teeth are axially provided in both parts of the groove 59 provided in the closing direction side, thus forming a tooth portion 61. Both side surfaces that define the groove 59 constitute a pair of electrode receiving surfaces 62 that are inclined from the closing direction toward both sides in the width direction. A recessed mating receptacle 63 which is open toward the closing direction axially extends in a bottom portion that defines the groove 59.

It is to be noted that the closing direction of the electrode member 48 indicates a side on which the electrode member 48 closely faces the probe 29. Moreover, the opening direction of the electrode member 48 indicates a side of the electrode member 48 away from the probe 29, for example, an upper surface side of the electrode member 48 or a back surface 33*a* side of the grip member 33.

The pad member 49 is softer than the probe 29, and is made of an insulating material having biocompatibility, for example, polytetrafluorethylene. The pad member 49 is mated with the mating receptacle 63 of the electrode member 48. The part of the pad member 49 on the closing-direction side protrudes from the electrode member 48 in the closing direction, thus forming an abutting receptacle 66. In the cross section orthogonal to the axial direction, the abutting receptacle 66 has a recessed shape corresponding to the projecting shape of the abutting portion 43 of the treatment section 32. When the grip member 33 is closed relative to the treatment section 32, the abutting portion 43 of the treatment section 32 abuts on and engages with the abutting receptacle 66 of the pad member 49. The pair of electrode surfaces 46 of the treatment section 32 are arranged parallel to the pair of electrode receiving surfaces 62 of the electrode section 58, and a clearance is maintained between the electrode section 58 and the treatment section 32. Consequently, the pad member 49 is disposed in the grip member 33 to face the treatment section 32. The pad member 49 abuts on the treatment section 32, when the grip member 33 closes relative to the treatment section 32.

Figure 7A:
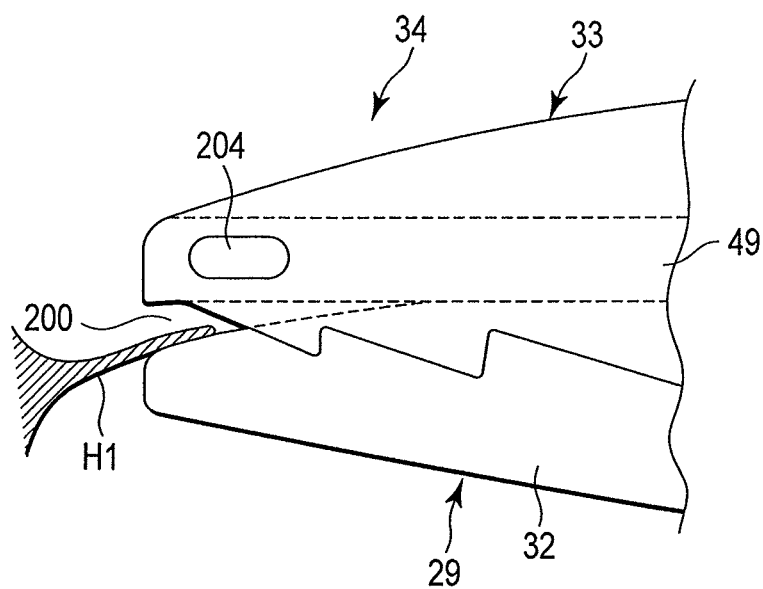
FIG. 7A is a side view showing that the distal grip section of the surgical treatment instrument is going to grip living tissue, while any protruding portion is not disposed.

It is to be noted that a distal end portion side of the surface of the treatment section 32 of the present embodiment which faces at least the grip member 33 is curved toward the central axis of the probe 29, specifically toward the bottom surface of the distal end portion side of the treatment section 32, toward the distal end, to achieve the enhancement of removing properties in the treatment section 32 relative to the living tissue and the decrease of cavitations in the treatment section 32. The central axis of the probe 29 is positioned on the downside of the surface facing the grip member 33, i.e., on a bottom surface side. At this time, the treatment section 32 is gently curved, for example, from the proximal end portion to the distal end portion of the treatment section 32. Therefore, when the grip member 33 closes relative to the treatment section 32, a space 200 is formed between a linear distal end portion of the grip member 33 and the curved distal end portion side of the treatment section 32 as shown in FIG. 7A, because the treatment section 32 is curved as described above. The treatment section 32 is curved, and hence this space 200 is surely generated and is not filled, even when the grip member 33 closes relative to the treatment section 32. Consequently, when living tissue H1 is gripped by the distal end portions, the living tissue cannot be gripped (picked) with excellent operation properties sometimes. Moreover, when the living tissue H1 is gripped by the grip member 33 and the treatment section 32, the ultrasonic vibration is transmitted to the living tissue H1, whereby the living tissue H1 slips down from the treatment section 32 and the grip member 33 owing to the ultrasonic vibration sometimes.

Figure 3:
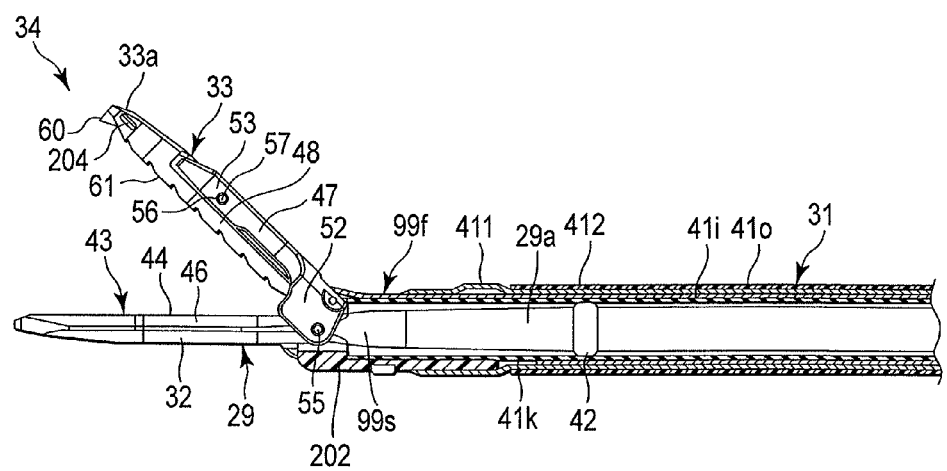
FIG. 3 is a partial longitudinal sectional side view showing the distal grip section according to the first embodiment of the present invention in an open state.
Figure 7B:
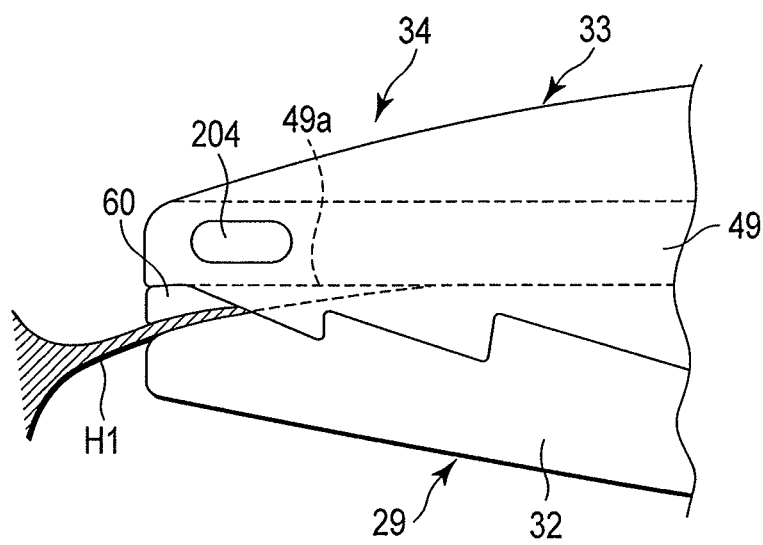
FIG. 7B is a side view showing that the living tissue is gripped by the distal grip section of the surgical treatment instrument according to the first embodiment of the present invention.

Therefore, as shown in FIG. 3, FIG. 4 and FIG. 7B, a distal end portion of the pad member 49 which faces the treatment section 32 includes a protruding portion 60 which protrudes toward the treatment section 32. In other words, the distal end portion of the pad member 49 includes the protruding portion 60 which protrudes from the distal end portion of the pad member 49 toward the distal end portion of the treatment section 32 in the opening/closing direction of the grip member 33, to fill in the space 200. Specifically, as shown in FIG. 7B, the pad member 49 has a planar facing surface 49a which faces the treatment section 32 and which is disposed substantially parallel to a longitudinal direction of the treatment section 32. Moreover, the protruding portion 60 protrudes from a distal end portion of the facing surface 49a toward the distal end portion of the treatment section 32, and is disposed in the distal end portion of the facing surface 49a to fill in the space 200. The protruding portion 60 is formed along a shape of the distal end portion of the treatment section 32. The protruding portion 60 may be pointed to be tapered toward the treatment section 32.

Therefore, when the grip member 33 is closed relative to the treatment section 32, the protruding portion 60 fills in the space 200 to abut on the distal end portion of the treatment section 32 along the shape of the distal end portion of the treatment section 32. Moreover, as shown in FIG. 7B, when the grip member 33 closes so that the living tissue H1 is gripped by the grip member 33 together with the treatment section 32, the protruding portion 60, together with the distal end portion of the treatment section 32, picks the living tissue. At this time, the protruding portion 60 abuts on the living tissue H1, and a strong pressure is applied to the living tissue H1 via the protruding portion 60. Consequently, the protruding portion 60 and the treatment section 32 securely grip the living tissue H1, and the treatment section 32 and the grip member 33 securely grip the living tissue H1 via the protruding portion 60. Moreover, when the treatment section 32 and the grip member 33 grip the living tissue H1, the protruding portion 60 abuts on the living tissue H1, and the strong pressure is applied to the living tissue H1 via the protruding portion 60. Therefore, even when the ultrasonic vibration is transmitted from the treatment section 32 to the living tissue H1, the slip-down of the living tissue H1 from the treatment section 32 and the grip member 33 is prevented.

It is to be noted that the distal end portion of the treatment section 32 of the present embodiment on at least a side facing the pad member 49 has a tapered region. Moreover, the protruding portion 60 is formed to extend along the tapered region of the treatment section 32. In other words, the distal end portion side of the treatment section 32 on at least the side facing the pad member 49 has a tapered shape in the axial direction. That is, the distal end portion side of the treatment section 32 is tapered toward the distal end portion. Therefore, the protruding portion 60 is formed to extend along this tapered shape in the axial direction.

Moreover, as described above and shown in FIG. 7B, the protruding portion 60 is formed to extend along the curved distal end portion side of the treatment section 32. At this time, the tapered region of the treatment section 32 and a tapered region of the protruding portion 60 are formed so that a radius of curvature of the tapered region of the treatment section 32 becomes approximately the same as that of the surface of the treatment section 32 which faces the tapered region of the protruding portion 60. In other words, the curved distal end portion side of the treatment section 32 and the corresponding portion of the protruding portion 60 corresponding to the curved distal end portion side of the treatment section 32 have approximately the same curvature. Moreover, the protruding portion 60 is formed to extend along the tapered shape in the axial direction as described above. At this time, the distal end portion side of the treatment section 32 having the tapered shape and the corresponding portion of the protruding portion 60 corresponding to the tapered shape have approximately the same curvature. Consequently, the curvature of the protruding portion 60 is approximately the same as that of the distal end portion side of the treatment section 32.

Here, the inner sheath 41i, the body member 47 and the electrode member 48 are electrically connected to one another, and constitute the first electrical path 99f for a high-frequency treatment. The electrode section 58 of the electrode member 48 functions as one of bipolar electrodes for the high-frequency treatment.

On the other hand, the probe 29 constitutes the second electrical path 99s for the high-frequency treatment. The treatment section 32 provided to the distal end portion of the probe 29 functions as the other of the bipolar electrodes used for the high-frequency treatment. As described above, the probe 29 is held to the inner sheath 41i by the insulating rubber lining 42, and the clearance is maintained between the inner sheath 41i and the probe 29. Moreover, the inner peripheral surface of the inner sheath 41i is provided with the insulating tube 41k. This prevents a short circuit between the inner sheath 41i and the probe 29.

Next, a gripping method of the living tissue H1 or living tissue H2 by use of the protruding portion 60 will be described with reference to FIG. 7A, FIG. 7B, FIG. 8A, and FIG. 8B.

The space 200 generated between the distal end portion of the grip member 33 and the distal end portion of the treatment section 32 as shown in FIG. 7A is filled with the protruding portion 60 as shown in FIG. 7B. Therefore, when the endmost portion of the distal grip section 34 (the treatment section 32 and the grip member 33) grips the thin living tissue H1, the protruding portion 60, together with the distal end portion of the treatment section 32, picks the living tissue. At this time, the protruding portion 60 abuts on the living tissue H1, and the strong pressure is applied to the living tissue H1 via the protruding portion 60. Consequently, as shown in FIG. 7B, the protruding portion 60 and the treatment section 32 securely grip the living tissue H1, and the treatment section 32 and the grip member 33 securely grip the living tissue H1 via the protruding portion 60. Moreover, when the treatment section 32 and the grip member 33 grip the living tissue, the protruding portion 60 abuts on the living tissue H1, and the strong pressure is applied to the living tissue H1 via the protruding portion 60. Therefore, even when the ultrasonic vibration is transmitted from the treatment section 32 to the living tissue, the slip-down of the living tissue from the treatment section 32 and the grip member 33 is prevented. That is, the living tissue H1 is firmly gripped without slipping.

Figure 8A:
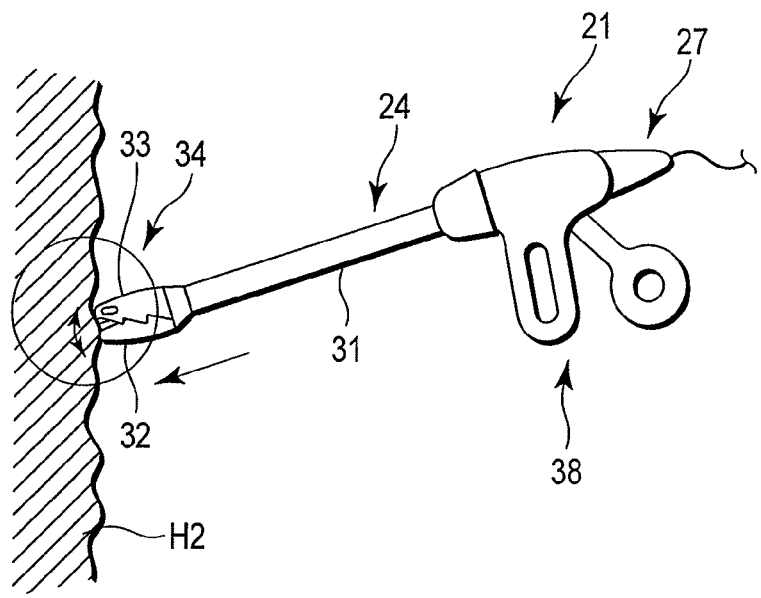
FIG. 8A is a side view showing that the protruding portion of the distal grip section of the surgical treatment instrument according to the first embodiment of the present invention perpendicularly approaches the living tissue.
Figure 8B:
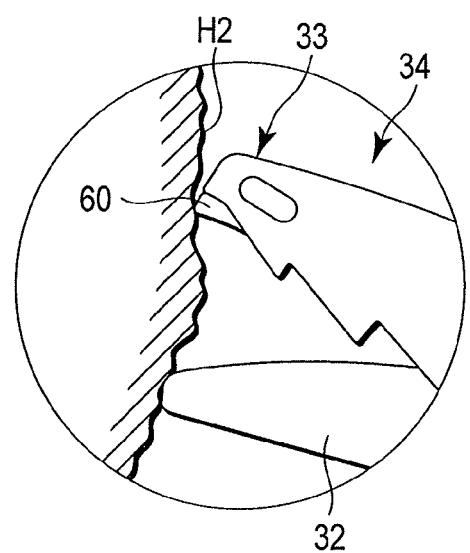
FIG. 8B is an enlarged side view of a part where the protruding portion of the distal grip section of the surgical treatment instrument according to the first embodiment of the present invention perpendicularly approaches the living tissue.

Moreover, as shown in FIG. 8A and FIG. 8B, even when the distal grip section 34 (the treatment section 32 and the grip member 33) substantially perpendicularly approach the living tissue H2, the living tissue H2 is firmly gripped by the protruding portion 60 without slipping in the same manner as described above.

The function of the surgical treatment system is described with reference to FIG. 6.

The surgical treatment system, when normally used, carries out a coagulation/cutting treatment or a coagulation treatment on living tissue.

That is, when the surgical treatment system is used to carry out the coagulation/cutting treatment, the living tissue is gripped by the distal grip section 34, and the cutting switch 39a of the handle unit 26 is depressed. The depression of the cutting switch 39a is detected by a switch detection section 68, and a cutting operation signal is output from the switch detection section 68 to a control section 69. The control section 69 to which the cutting operation signal is input is configured to control an ultrasonic waveform output section 71 and a high-frequency output section 72. The ultrasonic waveform output section 71 is configured to output a drive signal to the ultrasonic vibrator 28, and ultrasonic vibration is generated in the ultrasonic vibrator 28. The ultrasonic vibration generated in the ultrasonic vibrator 28 is transmitted by the probe 29, and the treatment section 32 at the distal end portion of the probe 29 is ultrasonically vibrated in contact with the gripped living tissue.

On the other hand, the high-frequency output section 72 is configured to apply a high-frequency voltage between the electrode section 58 and the treatment section 32 via the first and second electrical paths 99*f* and 99*s*, and a high-frequency current is passed through the gripped living tissue. Thus, both ultrasonic vibration and high-frequency current are used to carry out, on the living tissue gripped by the distal grip section 34, a coagulation/cutting treatment that provides excellent cutting and coagulation functions. In order to carry out the coagulation treatment, the coagulation switch 39*b* of the handle unit 26 is depressed. In this case, a coagulation operation signal is output from the switch detection section 68 to the control section 69. The high-frequency output section 72 is controlled by the control section 69 so that a high-frequency current is passed through the living tissue gripped by the distal grip section 34. In this way, the high-frequency current is used to carry out, on the living tissue gripped by the distal grip section 34, the coagulation treatment that provides an excellent coagulation function.

The surgical treatment system according to the present embodiment has the following advantageous effects.

In the present embodiment, as shown in FIG. 7B, the space 200 generated between the distal end portion of the grip member 33 and the distal end portion of the treatment section 32 can be filled with the protruding portion 60. Moreover, in the present embodiment, when the living tissue H1 is gripped by the treatment section 32 and the grip member 33 as shown in FIG. 7B, the protruding portion 60 can abut on the living tissue H1. The living tissue can be gripped by the protruding portion 60 and the distal end portion of the treatment section 32, and the strong pressure can be applied to the living tissue H1 via the protruding portion 60. Consequently, according to the present embodiment, the living tissue H1 can securely be gripped by the protruding portion 60 with excellent operation properties. Further in the present embodiment, when the living tissue H1 is gripped by the treatment section 32 and the grip member 33, the protruding portion 60 can abut on the living tissue H1, and the strong pressure can be applied to the living tissue H1 via the protruding portion 60. Therefore, even when the ultrasonic vibration is transmitted from the treatment section 32 to the living tissue H1, it is possible to prevent the slip-down of the living tissue H1 from the treatment section 32 and the grip member 33.

Consequently, according to the present embodiment, the protruding portion 60 can securely grip the living tissue H1 with excellent operation properties, and can prevent the slip-down of the living tissue H1. Therefore, usability during the gripping can be enhanced. Further in the present embodiment, the living tissue H1, in this state, does not have to be gripped again, but can be subjected to the coagulation/cutting treatment or the coagulation treatment.

Moreover, in the present embodiment, as shown in FIG. 8A and FIG. 8B, even when the distal grip section 34 substantially perpendicularly approaches the living tissue H2, the living tissue H2 can firmly be gripped without slipping. It is possible to prevent the slip-down of the living tissue.

Furthermore, in the present embodiment, when the treatment section 32 is curved, it is possible to obtain the above effects, while achieving the enhancement of the removing properties of the living tissue in the treatment section 32 and the decrease of the cavitations in the treatment section 32.

Further in the present embodiment, as shown in FIG. 7B, the protruding portion 60 is formed to extend along the shape of the curved distal end portion side of the treatment section 32 in the axial direction, and hence the living tissue H1 can be picked. The living tissue H1 can securely be gripped by the protruding portion 60 with the excellent operation properties, and the slip-down of the living tissue H1 can be prevented. Consequently, even the small living tissue H1 can be gripped according to the present embodiment.

Figure 7C:
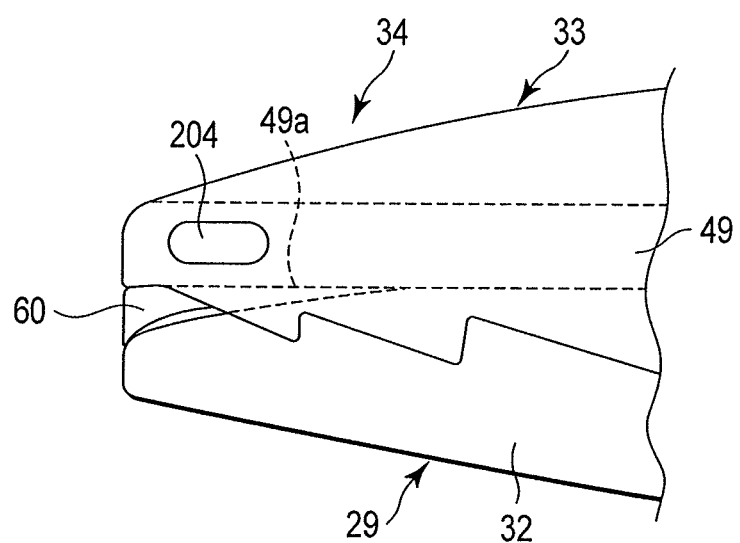
FIG. 7C is a side view showing that a curvature of the protruding portion is smaller than that of a distal end portion side of the treatment section.

Additionally, in the present embodiment, the curvature of the protruding portion 60 is approximately the same as that of the distal end portion side of the treatment section 32 as shown in FIG. 7B, and hence the living tissue can securely be gripped by the protruding portion 60 with the excellent operation properties. The slip-down of the living tissue can be prevented. It is to be noted that the protruding portion 60 may be formed so that the radius of curvature of the surface of the protruding portion 60 which faces the tapered region becomes smaller than that of the tapered region of the treatment section 32. In other words, the curvature of the protruding portion 60 may be smaller than that of the distal end portion side of the treatment section 32 as shown in FIG. 7C. Consequently, it is also possible to obtain effects similar to the above effects.

It is to be noted that the protruding portion 60 may be disposed in at least one of the distal end portion of the pad member 49 and the distal end portion of the treatment section 32. Moreover, protruding portions 60 may be arranged in the width direction orthogonal to the longitudinal direction of the grip member 33.

Furthermore, the protruding portion 60 does not necessarily have to be formed to extend along the shape of the distal end portion of the treatment section 32, as long as it is possible to fill in the space 200. The protruding portion may overlap with the distal end portion of the treatment section 32. Consequently, according to the present embodiment, the living tissue can be picked with a stronger force.

Second Embodiment

A second embodiment of the present invention will be described with reference to FIG. 4.

A grip member 33 of the present embodiment includes a tooth portion 61 in the same manner as in the first embodiment. That is, the tooth portion 61 of the present embodiment includes teeth formed along a longitudinal direction of the grip member 33 in the same manner as in the first embodiment.

The teeth are arranged also in the vicinity of a protruding portion 60. For example, in a width direction, the protruding portion 60 and the tooth disposed in the most distal end portion are arranged on the same line.

A pitch B between the tooth and the tooth on a distal end portion 61B side of the tooth portion 61 is smaller than a pitch A between the tooth and the tooth on a proximal end portion 61A side of the tooth portion 61. These pitches A and B are, for example, from 0.1 to 1 mm. For example, the pitch is large from the proximal end portion 61A to a desirable portion, and is small from the desirable portion to the distal end portion 61B. It is to be noted that the pitch may gradually and continuously become small from the proximal end portion 61A side toward the distal end portion 61B side.

Consequently, when living tissue H2 is gripped in the present embodiment, engagement between the living tissue H2 and the tooth portion 61 strengthens on the distal end portion 61B side, because the pitch B is smaller than the pitch A. Therefore, in the present embodiment, the living tissue can securely be gripped by the distal end portion 61B side with excellent operation properties, and it is possible to prevent the slip-down of the living tissue from the treatment section 32 and the grip member 33. Moreover, according to the present embodiment, the living tissue, in this state, does not have to be gripped again, but can be subjected to a coagulation/cutting treatment or a coagulation treatment.

Moreover, when the living tissue is gripped by the whole surface of the treatment section 32 and the whole surface of the grip member 33, a sufficient contact area with the living tissue can be maintained on the proximal end portion 61A side while the living tissue is securely gripped on the distal end portion 61B side, because the pitch A is larger than the pitch B. Consequently, according to the present embodiment, the stable coagulation/cutting treatment or coagulation treatment can be performed on the gripped living tissue.

Hereinafter, modifications of the embodiments will be described.

[Modification 1]

Modification 1 is described with reference to FIG. 9, FIG. 10, FIG. 11, FIG. 12, FIG. 13 and FIG. 14. In Modification 1, as shown in FIG. 11, a surgical treatment instrument 101 includes two units, i.e., a vibrator unit 102 including therein an ultrasonic vibrator, and a handle unit 104 integral with a probe unit 103. It is to be noted that the probe unit 103 and the handle unit 104 may be separate units. The two units are detachably coupled to one another. The vibrator unit 102 is detachably screwed with a proximal end portion of the handle unit 104 by a torque wrench 141. At this time, an adapter 151 is used. When the vibrator unit 102 is attached to or detached from the proximal end portion of the handle unit 104, the adapter 151 is attached to the outer peripheral surface of the vibrator unit 102, and is used to fix and hold the vibrator unit 102 by a surgeon.

When the vibrator unit 102 is attached to the handle unit 104 by the torque wrench 141, the torque wrench 141 is engaged with a rotary knob 131 provided in the proximal end portion of the probe unit 103 as shown in FIG. 11. When the torque wrench 141 turns in an arrow direction of FIG. 11, it is necessary to grip and fix, for example, the vibrator unit 102 so that the vibrator unit 102 does not turn in the same direction. At this time, the adapter 151 is used. The adapter 151 is attached to the vibrator unit 102, and the adapter 151 is gripped by the surgeon so that the vibrator unit 102 does not turn, whereby the vibrator unit 102 is fixed.

Figure 9:
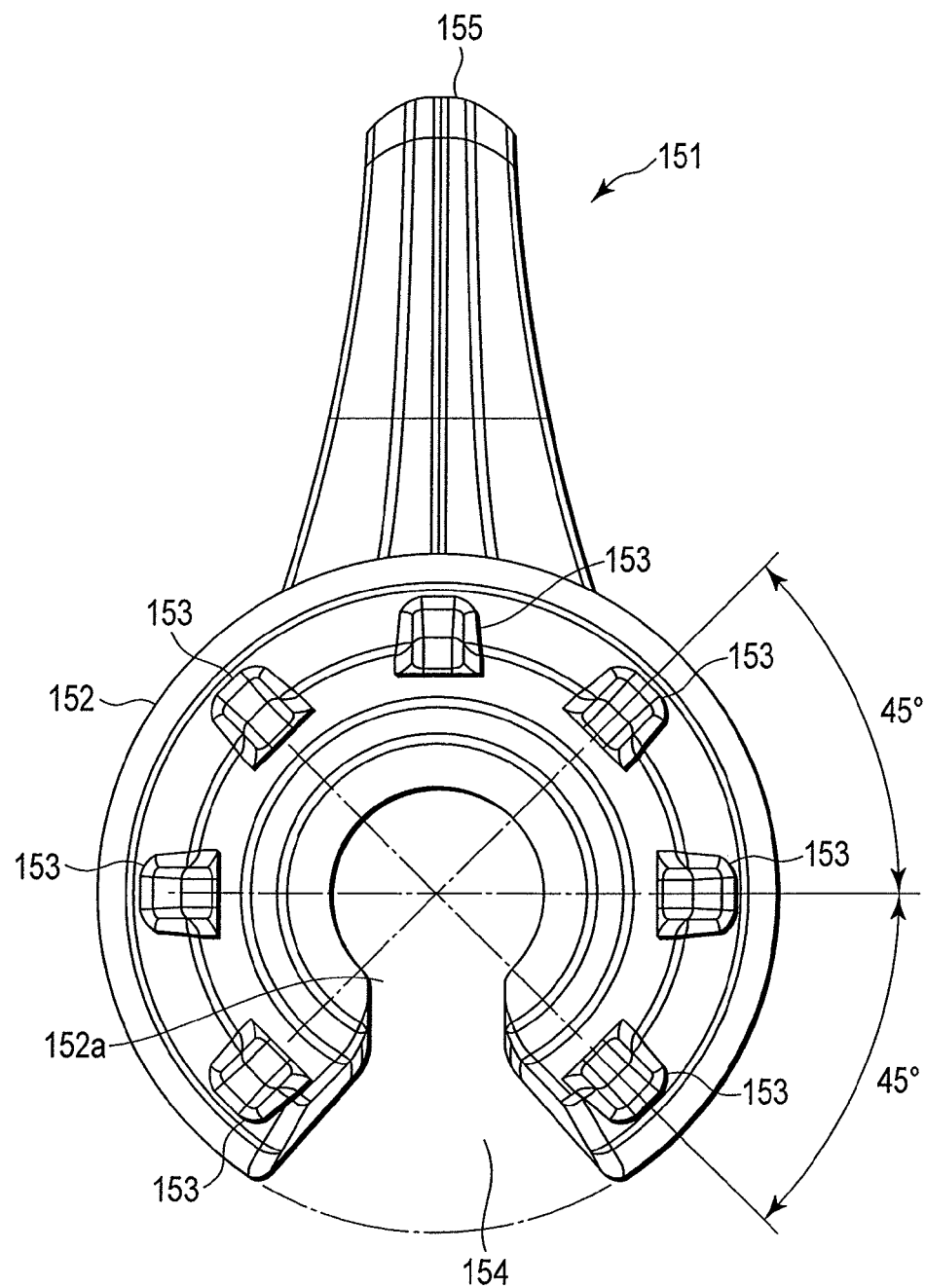
FIG. 9 is a front view of an adapter for use in modification 1 of the present invention seen from a direction of a vibrator unit.

As shown in FIG. 9 and FIG. 10, the adapter 151 is provided with a cylindrical portion 152 for receiving the vibrator unit 102. The cylindrical portion 152 of the adapter 151 has therein a space portion 152a. The inner peripheral surface of the cylindrical portion 152 is provided with recess portions 153 extending in a longitudinal axis direction of the adapter 151. Seven recess portions 153 are provided at substantially equal intervals (e.g., 45-degree intervals) in a peripheral direction.

Moreover, the adapter 151 engages with a vibrator cover 107 of the vibrator unit 102. The outer peripheral surface of the vibrator cover 107 is provided with protruding portions 107a extending in the longitudinal axis direction as shown in FIG. 11. Four protruding portions 107a are provided at substantially equal intervals in the peripheral direction. The protruding portions 107a engage with the recess portions 153.

Furthermore, as shown in FIG. 9, the adapter 151 is provided with a cutout portion 154 formed by cutting part of a round shape in a peripheral wall of the cylindrical portion 152. In addition, the outer peripheral surface of a proximal end portion of the adapter 151 is provided with a projecting portion 155 extending in an outward direction.

Next, a way to use the adapter 151 will be described with reference to FIG. 12, FIG. 13 and FIG. 14. There is carried out an assembling operation of the vibrator unit 102 of the surgical instrument 101 with the handle unit 104 in order as shown by arrows of FIG. 12.

(1) The vibrator unit 102 is inserted into the handle unit 104, and the rotary knob 131 is turned with fingers in a fastening direction (clockwise) until the knob 131 lightly stops, while the vibrator unit 102 is held by the handle unit 104.

(2) The adapter 151 is attached to the outer peripheral surface of the vibrator unit 102.

(3) The torque wrench 141 is attached to the rotary knob 131.

The vibrator unit 102 is provided with a cable 109 for supplying a drive current to the vibrator unit 102. However, the adapter 151 is provided with the cutout portion 154. Therefore, the cable passes through the cutout portion 154, whereby the adapter 151 is attached to the outer periphery of the vibrator unit 102.

The cable 109 is guided into the space portion 152a through the cutout portion 154, and then the adapter 151 is attached to the outer periphery of the vibrator unit 102 so that positions of the recess portions 153 are aligned with those of the protruding portions 107a. Consequently, the recess portions 153 engage with the protruding portions 107a, whereby the movement of the adapter 151 relative to the vibrator unit 102 in a turning direction is regulated.

Figure 14:
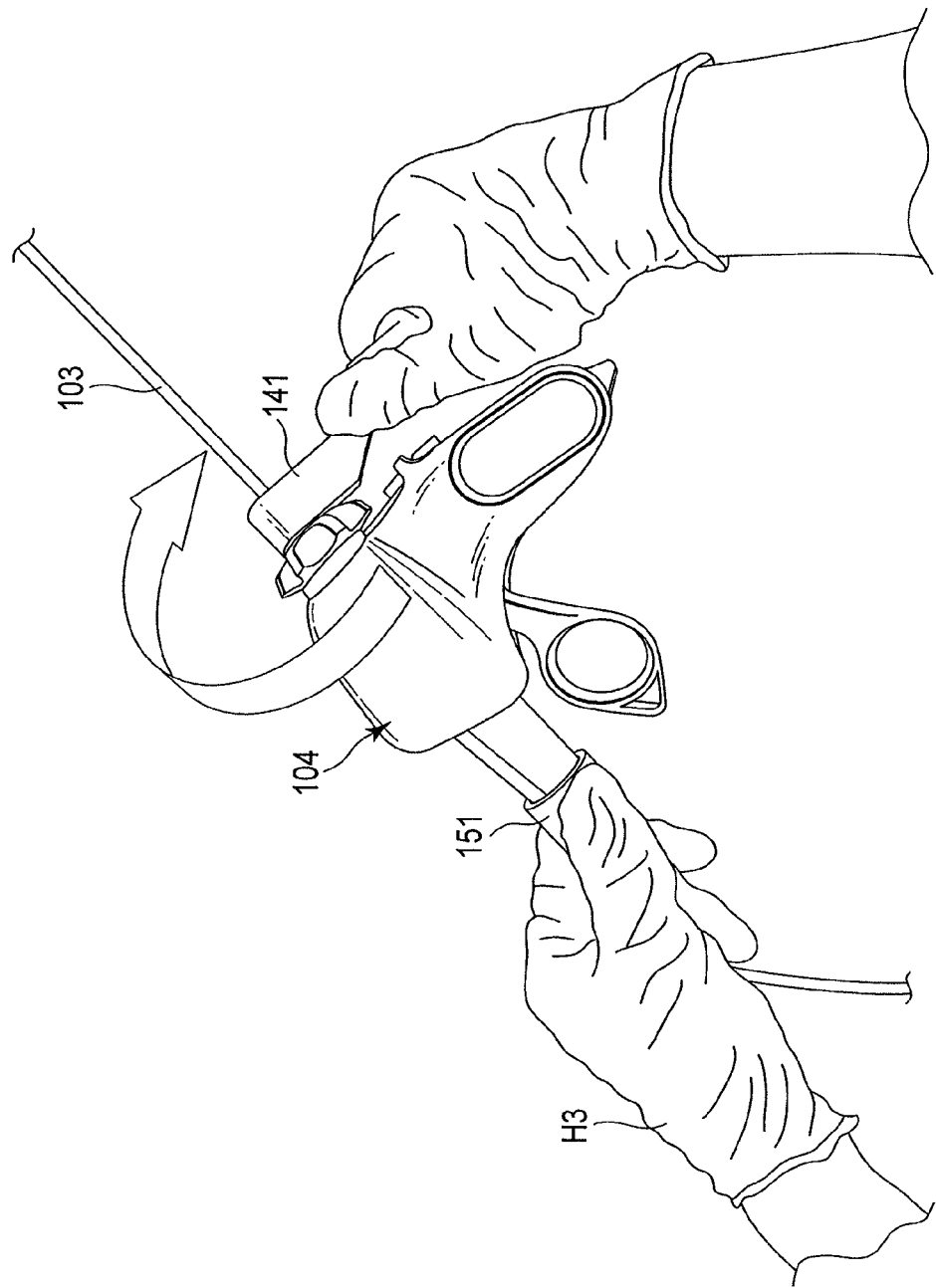
FIG. 14 is an explanatory view for explaining the assembling operation of the surgical treatment instrument of modification 1.

As shown in FIG. 14, when the adapter 151 is attached to the vibrator unit 102, the outer periphery of the adapter 151 and the projecting portion 155 thereof are gripped. Consequently, the movement of the vibrator unit 102 relative to the probe unit 103 in the turning direction is fixed, and the torque wrench 141 is turned in the fastening direction (clockwise) to apply a turning torque to the probe unit 103. Consequently, the probe unit 103 can be fastened and fixed to the vibrator unit 102. For example, the vibrator unit 102 is held with the fingers while attaching the projecting portion 155 to palm H3. Consequently, the movement of the vibrator unit 102 in the turning direction can more easily be regulated.

Thus, in the present modification, even when the turning force is applied by the torque wrench 141, it is possible to prevent, by the adapter 151, the vibrator unit 102 from turning in the surgeon's hands.

Moreover, in the present modification, when more recess portions 153 than the protruding portions 107a are arranged, the recess portions 153 can easily be combined with the protruding portions 107a. The adapter 151 can be attached to the vibrator unit 102 at various angles (turning angles around a longitudinal axis of the vibrator unit 102).

Furthermore, in the present modification, the adapter 151 can easily be attached to the outer peripheral surface of the vibrator unit 102 through the cutout portion 154, without being influenced by the cable 109.

Additionally, in the present modification, the adapter 151 can easily be gripped by the projecting portion 155.

[Modification 2]

As shown in FIG. 2 and as described above, a probe 29 is inserted through an insertion sheath 31, and a distal end portion of the probe 29 is projected from a distal end opening of the insertion sheath 31. On the outer peripheral surface of the distal end portion of the probe 29, a regulating section 202 is disposed to regulate a projecting length of the distal end portion of the probe 29 from the distal end opening. To regulate the projecting length, the regulating section 202 engages with an inner sheath 41*i*, and is fixed to the inner sheath 41*i*.

Consequently, according to the present modification, the projecting length of the distal end portion of the probe 29 can accurately be regulated by the regulating section 202. Further in the present modification, the regulating section 202 can prevent the probe 29 from coming in contact with the inner sheath 41*i*.

[Modification 3]

As shown in FIG. 2, the regulating section 202 is a resin material. The regulating section 202 is also a contact preventing section which prevents contact between an inner sheath 41*i* and a probe 29 and prevents the probe 29 from contacting and breaking the inner sheath 41*i* through ultrasonic vibration.

Consequently, according to the present modification, it is possible to prevent, by the regulating section 202, the probe 29 from contacting and breaking the inner sheath 41*i* through the ultrasonic vibration.

[Modification 4]

As shown in FIG. 2, air tightness between an insulating tube 41*k* and a probe 29 is acquired by a rubber lining 42. Consequently, according to the present modification, it is possible to decrease parts for the air tightness.

It is to be noted that the insulating tube 41*k* is inserted under pressure into the rubber lining 42, to be fixed. Consequently, according to the present modification, it is possible to decrease parts for the fixing.

[Modification 5]

As shown in FIG. 2, an outer sheath 410 includes a metal pipe 411 and a resin tube 412 which covers the metal pipe. The metal pipe 411 is longer than the resin tube 412, and a distal end portion of the metal pipe 411 is exposed from a distal end portion of the resin tube 412. The distal end portion of the metal pipe 411 swells diametrically as compared with the resin tube 412, to prevent the resin tube 412 from being turned up.

Consequently, according to the present modification, the insulating resin tube 412 can be prevented from being turned up, by the distal end portion of the metal pipe 411 which swells diametrically, even when an insertion sheath 31 moves in an axial direction.

[Modification 6]

In a probe 29, a portion other than a portion required to pass electricity through the probe 29 is coated to prevent living tissue from sticking to this portion. As shown in FIG. 2, this portion is, for example, a portion 29*a* inserted into an insertion sheath 31.

Consequently, according to the present modification, the coating can prevent the living tissue from sticking to the portion (the portion 29*a*) other than the portion required to pass the electricity through the probe 29.

[Modification 7]

As shown in FIG. 2, a back surface 33*a* of a grip member 33 is coated with an insulating material, to prevent a current from flowing from the back surface 33*a* to a patient through living tissue.

Consequently, according to the present modification, the coating can prevent the current from flowing from the back surface 33*a* of the grip member 33 to the patient through the living tissue.

[Modification 8]

As shown in FIG. 4, an electrode member 48 includes an opening 204 in which a distal end portion of a pad member 49 is caught, to prevent the pad member 49 from coming off the electrode member 48. The opening 204 is, for example, a lateral hole formed through the side surface of the electrode member 48.

Consequently, according to the present modification, the pad member 49 can be prevented from coming off the electrode member 48, when the distal end portion of the pad member 49 is caught in the opening 204.

[Modification 9]

In an electrode member 48 of a grip member 33, an electrode receiving surface 62 which is the inner surface of the grip member 33 as shown in FIG. 5 is plated with a conductive and super water-repellent material to prevent living tissue from sticking to the electrode receiving surfaces 62. Moreover, the outer peripheral surface of the grip member 33 excluding the electrode receiving surfaces 62 and including a back surface 33*a* is coated with an insulating material, to prevent a current from flowing from the outer peripheral surface into a patient through the living tissue.

Consequently, according to the present modification, the super water-repellent plating can prevent the living tissue from sticking to the electrode receiving surfaces 62, and the coating can prevent the current from flowing from the outer peripheral surface through the living tissue.

[Modification 10]

A surgical treatment instrument 21 is accommodated in a sterilization tray 206 as shown in FIG. 15A, and the sterilization tray 206 is covered with a sheet 208 to cover the surgical treatment instrument 21 as shown in FIG. 15B. The sterilization tray 206 and surgical treatment instrument 21 covered with the sheet 208 are sterilized. At this time, the whole sheet 208 is sterilized. In the surgical treatment instrument 21, a rotary knob 210 having a protruding/recess shape is diametrically larger than a handle unit 26. Consequently, when the surgical treatment instrument 21 is accommodated in the sterilization tray 206 as shown in FIG. 15B, the rotary knob 210 rattles (rotates). Therefore, the surgical treatment instrument 21 rattles in the sterilization tray 206 to damage the surgical treatment instrument 21 sometimes. Moreover, when the sterilization tray 206 is covered with the sheet 208, as shown in FIG. 15B, the sheet 208 contacts the rotary knob 210, to frictionally damage the sheet 208 sometimes.

Therefore, as shown in FIG. 15C, the sterilization tray 206 includes a recess portion 212 to receive the rotary knob 210 so that the rotary knob 210 is fixed, thereby preventing the rattling of the surgical treatment instrument 21 and preventing the contact between the sheet 208 and the rotary knob 210. The recess portion 212 has approximately the same shape as the rotary knob 131, and is disposed at a position corresponding to the rotary knob 131. The recess portion 212 includes a protruding portion 214 caught by a recess portion 210*a* of the rotary knob 210.

Consequently, according to the present modification, the protruding portion 214 is caught by the recess portion 210*a*, whereby it is possible to prevent the rattling of the surgical treatment instrument 21, the damage of the surgical treatment instrument 21, the contact between the sheet 208 and the rotary knob 210, and the damage of the sheet 208. Therefore, in the present modification, it is possible to acquire a sterilized state in the sheet 208 and the sterilization tray 206.

[Modification 11]

As shown in FIG. 1, a handle unit 26 includes a holding cylinder 220. In the holding cylinder 220, a cylindrical contact point unit 222 is disposed as shown in FIG. 16A. The contact point unit 222 includes a cylindrical electrode holding member 224 made of resin. The electrode holding member 224 includes three electrode receiving portions 226 having different sizes, respectively, as shown in FIG. 16A and FIG. 16B. The electrode receiving portions 226 are assembled with electrode members 228. The electrode members 228 have such a shape as to engage with the electrode receiving portions 226, and have spring properties, so that assembling can be simplified and the number of parts can be decreased.

Consequently, according to the present modification, the electrode members 228 can simplify the assembling, and the number of the parts for the assembling can be decreased.

[Modification 12]

As shown in FIG. 16A, a cylindrical contact point unit 222 is attached to a contact point portion 28a on a proximal end portion side of an ultrasonic vibrator 28, to save a soldering step and enhance assembling properties.

Consequently, according to the present modification, the assembling can be simplified, and the number of parts for the assembling and assembling steps can be decreased.

[Modification 13]

As shown in FIG. 17, in a holding cylinder 220, an operation force transmission mechanism 230 is disposed to transmit an operation force of a movable handle 37 to an inner sheath 41i connected to a grip member 33.

The operation force transmission mechanism 230 mainly includes a cylindrical spring receiving member 232 mainly made of a metal, and a slider member 234 made of resin. The spring receiving member 232 is disposed along the same axis as the central axis of a holding cylinder 220, and extended in the same direction as an inserting direction of an insertion sheath 31.

On the outer peripheral surface of the spring receiving member 232, a coil spring 236, the slider member 234, a stopper 238 and a spring receptacle 240 are arranged. A front end portion of the coil spring 236 is fixed to the spring receptacle 240. The stopper 238 regulates a rear end side moving position of the slider member 234. The coil spring 236 is attached with a predetermined equipment capacity between the spring receptacle 240 and the slider member 234.

In the outer peripheral surface of the slider member 234, a ring-like engagement groove 242 is formed along a peripheral direction. In the engagement groove 242, an operation pin 244 of the movable handle 37 is inserted and engaged. When the movable handle 37 is gripped to close the movable handle 37 relative to a fixed handle 36, the operation pin 244 turns around a support pin 246 with a turning operation of the movable handle 37 at this time. The slider member 234 operated with the turning operation of the support pin 246 moves forward direction along an axial direction. At this time, the spring receiving member 232 coupled to the slider member 234 via the coil spring 236 also moves back and forth together with the slider member 234. To a distal end portion of the spring receiving member 232, there are fixed a pair of engagement pins 248 for use in attaching or detaching a sheath unit 24 to or from a handle unit 26 side. Consequently, the operation force of the movable handle 37 is transmitted to the sheath unit 24 via the pair of engagement pins 248, to open or close the grip member 33.

Between the engagement groove 242 formed in the slider member 234 and the operation pin 244 engaged with the engagement groove 242, a lessening member 250 is disposed to lessen the turning of the rotary knob 210 with the moving of the slider member 234. The lessening member 250 is disposed in, for example, the engagement groove 242. The lessening member 250 is made of, for example, low-creep PTFE.

Consequently, according to the present modification, the lessening member 250 can lessen the turning of the rotary knob 210.

[Modification 14]

As shown in FIG. 17, a fixed handle 36 has a ring-like shape such that a surgeon can grip the fixed handle 36. On the outer peripheral surface of the fixed handle 36, there are further disposed recess portions 252 in which fingers can be caught when a surgeon grips the fixed handle 36.

Consequently, according to the present modification, it is possible to enhance operation properties and gripping properties, because the fingers can be caught in the recess portions 252.

[Modification 15]

As shown in FIG. 17, in the fixed handle 36, there are arranged a substrate for a switch section 38 (a cutting switch 39a and a coagulation switch 39b), and a soft member 254 made of, for example, resin or the like and disposed between the substrate and the switch section 38 to enhance an operation capacity of the switch section 38. The soft member 254 can enhance the operation capacity of the switch section 38, to prevent a wrong operation of the switch section 38.

Consequently, according to the present modification, it is possible to enhance the operation capacity of the switch section 38 and prevent the wrong operation of the switch section 38 by the soft member 254.

[Modification 16]

As shown in FIG. 1, a movable handle 37 includes a substantially U-shaped arm portion 256 in an upper portion thereof. The U-shaped arm portion 256 includes two arms 256a and 256b. The movable handle 37 is assembled with a holding cylinder 220 while the holding cylinder 220 is inserted between the two arms 256a and 256b.

As shown in FIG. 1, each of the arms 256a and 256b include a support pin 246 and an operation pin 244. As shown in FIG. 18A, a pin receiving hole portion 258 and a window portion 260 are formed in both side portions of the holding cylinder 220. The support pins 246 of the arms 256a and 256b are inserted into the pin receiving hole portion 258 of the holding cylinder 220. Consequently, an upper end portion of the movable handle 37 is rotatably and pivotally supported by the holding cylinder 220 via the support pins 246.

The operation pins 244 of the movable handle 37 extend into the holding cylinder 220 through the window portion 260 of the holding cylinder 220.

As shown in FIG. 18B, the movable handle 37 includes a pin 262 in the vicinity of the operation pins 244. The pin 262 extends into the holding cylinder 220 through the window portion 260. As shown in FIG. 18A and FIG. 18B, in the holding cylinder 220, an elastic member 264 such as a leaf spring flipped by the pin 262 which moves with an opening/closing operation of the movable handle 37. The elastic member 264 is disposed along a movement line of the pin 262. When the elastic member 264 is flipped by the pin 262, for example, sound is generated. Consequently, a surgeon is notified of a grip amount of the movable handle 37.

Consequently, according to the present modification, the pin 262 moves toward the elastic member 264 with the opening/closing operation of the movable handle 37, whereby the elastic member 264 can be flipped by the pin 262, and the sound can be generated. Consequently, according to the present modification, the surgeon can be notified of the grip amount of the movable handle 37 by the sound.

[Modification 17]

Figure 19:
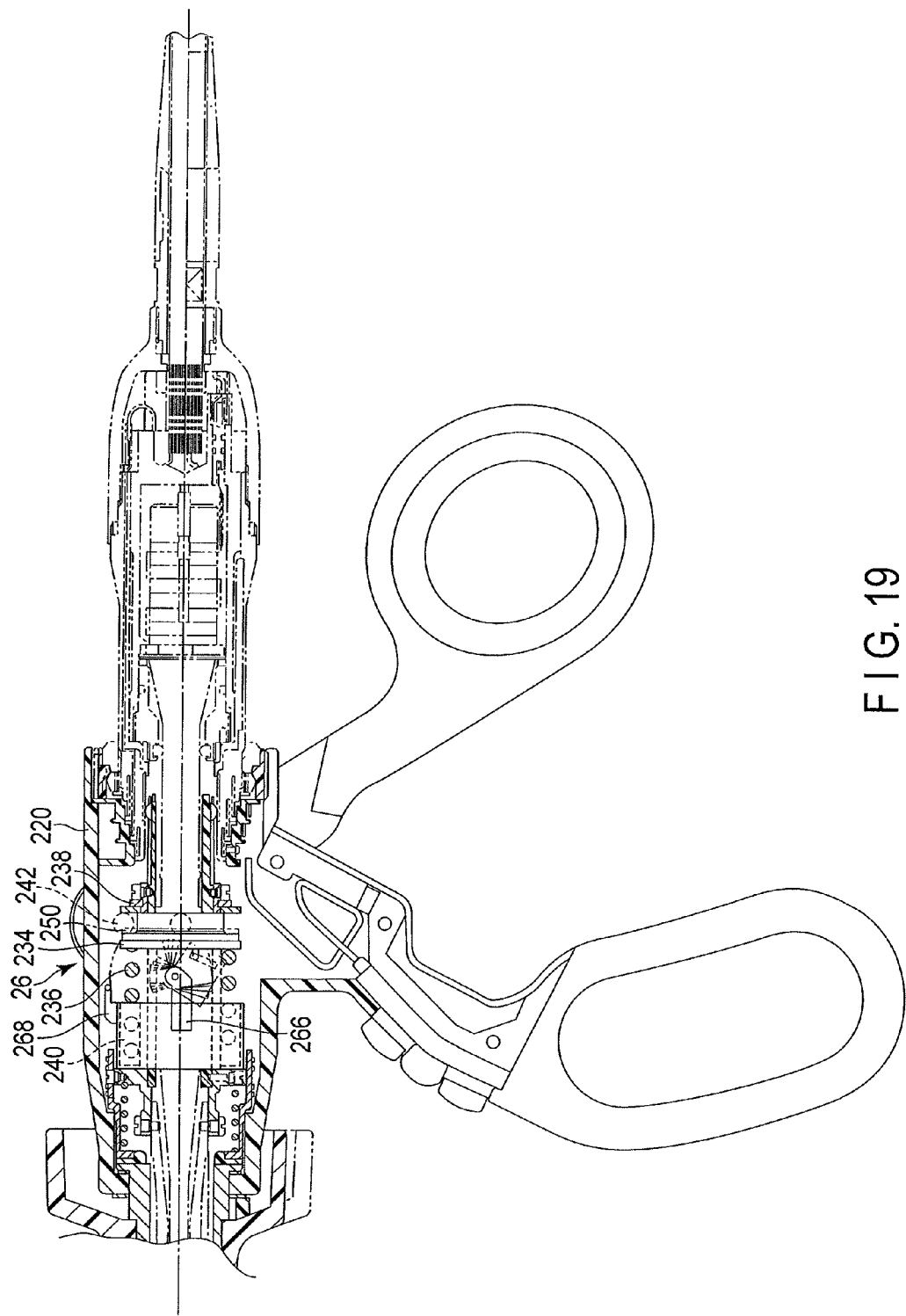
FIG. 19 is a view showing that the elastic member turns with the opening/closing operation of the movable handle, to flip the pin.

As shown in FIG. 19, in a holding cylinder 220, there are fixed an elastic member 266 such as a leaf spring which turns with the movement of a slider member 234 via a movable handle 37, and a pin 268 flipped by the turning elastic member 266. The elastic member 266 and the pin 268 are disposed in, for example, a spring receptacle 240. When the pin 268 is flipped by the elastic member 266, for example, sound is generated. Consequently, a surgeon is notified of a gripping amount of the movable handle 37.

Consequently, according to the present modification, the slider member 234 moves with the opening/closing operation of the movable handle 37. Moreover, the elastic member 266 turns with the movement of the slider member 234. Consequently, according to the present modification, the pin 268 can be flipped by the elastic member 266, and the sound can be generated. Consequently, according to the present modification, the surgeon can be notified of the gripping amount of the movable handle 37 by the sound.

[Modification 18]

As shown in FIG. 20, a slider member 234 includes a claw 270 at a distal end portion thereof. The claw 270 is formed integrally with the slider member 234, and moves together with the slider member 234. A spring receptacle 240 includes a film 272 flipped by the claw 270 which moves with the movement of the slider member 234. The film 272 is formed on the peripheral surface of the spring receptacle 240, and has a disc-like shape. When the film 272 is flipped by the claw 270, for example, sound is generated. Consequently, a surgeon is notified of a grip amount of a movable handle 37.

Consequently, according to the present modification, the film 272 can be flipped by the claw 270, and the sound can be generated. Therefore, according to the present modification, the surgeon can be notified of the grip amount of the movable handle 37 by the sound.

[Modification 19]

As shown in FIG. 21A and FIG. 21B, there is disposed a probe presser regulating section 275 including a tube 274 disposed in a distal end portion of the section to protect the surface of a probe 29 on a grip member 33 side and to prevent electricity from being passed between the probe 29 and an inner sheath 41i (a connecting portion with the grip member 33). The tube 274 may be separated from the probe presser regulating section 275. It is to be noted that as shown in FIG. 21C, the tube 274 may be formed integrally with the probe presser regulating section 275.

[Modification 20]

A distal end portion of an insulating tube 41k may, be squeezed and inserted into a probe 29 and a grip member 33.

[Modification 21]

As shown in FIG. 22, part of an inner sheath 41i is squeeze-processed toward a probe 29 to abut on the probe 29.

Consequently, according to the present modification, the inner sheath 41i can be fixed, and the number of parts for the fixing can be decreased. Moreover, in the present modification, air tightness can be acquired between the inner sheath 41i and the probe 29, and parts for the air tightness can be decreased.

[Modification 22]

A proximal end portion of a probe 29 inserted into a sheath unit 24 is coupled to the sheath unit 24 via, for example, a pin not shown, and the probe becomes integral with the sheath unit 24. The pin is disposed in a rotary knob 210 of a handle unit 26. Therefore, a torque is applied to the probe 29 and the sheath unit 24 by the handle unit 26 via the pin.

Consequently, according to the present modification, the probe 29 and the sheath unit 24 are formed integrally, so that assembling operations can be decreased, when a surgical instrument 21 is constituted of three structures of the probe 29, the sheath unit 24 and the handle unit 26. Moreover, in the present modification, when the rotary knob 210 is turned, the torque can be applied to the probe 29 and the sheath unit 24 via the pin.

The present invention is not limited to the above embodiments as it is, and in an implementing stage, constitutional elements can be modified and embodied without departing from the scope of the invention. Moreover, various invention can be formed by suitable combinations of the constitutional elements disclosed in the above embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic surgical instrument comprising:
an ultrasonic vibrator configured to generate ultrasonic vibration;
a vibration transmission section configured to transmit the ultrasonic vibration generated in the ultrasonic vibrator;
a treatment section formed in a distal end portion of the vibration transmission section, and configured to transmit the ultrasonic vibration from the ultrasonic vibrator to living tissue;
a grip member openably or closably provided relative to the treatment section;
a pad member provided at a position of the grip member which faces the treatment section; and
a planar facing surface disposed on the pad member, and disposed substantially parallel to a longitudinal direction of the treatment section while the grip member is closed,
wherein a distal end portion of the treatment section faces the pad member, and is curved from a proximal end portion side of the treatment section toward the distal end portion side of the treatment section in a direction away from the facing surface, and
the pad member includes a protruding portion which is disposed on the facing surface, protrudes from the facing surface toward the distal end portion of the treatment section, and abuts on the distal end portion of the treatment section while the grip member is closed.

2. The ultrasonic surgical instrument according to claim 1, wherein the distal end portion of the treatment section has a tapered region on at least a side facing the pad member, and
the protruding portion is formed to extend along the tapered region of the treatment section.

3. The ultrasonic surgical instrument according to claim 2, wherein the protruding portion is formed so that a radius of curvature of the surface of the protruding portion which faces the tapered region becomes smaller than that of the tapered region of the treatment section.

4. The ultrasonic surgical instrument according to claim 2, wherein the tapered region and the protruding portion are formed so that a radius of curvature of the tapered region of the treatment section is approximately the same as that of the surface of the protruding portion which faces the tapered region.

5. The ultrasonic surgical instrument according to claim 1, wherein the grip member comprises a tooth portion including teeth formed along a longitudinal axis direction of the grip member in a portion of the grip member on the side of the treatment section, and
the teeth are formed so that a pitch between the adjacent teeth on a proximal end portion side of the tooth portion is smaller than on a distal end portion side of the tooth portion.

6. The ultrasonic surgical instrument according to claim 5, wherein the pitch is from 0.1 to 1 mm.

* * * * *